(12) United States Patent
Zhuo et al.

(10) Patent No.: US 10,485,434 B2
(45) Date of Patent: Nov. 26, 2019

(54) NON-INVASIVE AND NON-OCCLUSIVE BLOOD PRESSURE MONITORING DEVICES AND METHODS

(71) Applicant: Angilytics Inc., Berkeley, CA (US)

(72) Inventors: Xiaoding Zhuo, Berkeley, CA (US); Piotr Przybyszewski, San Jose, CA (US)

(73) Assignee: ANGILYTICS, INC., Berkeley, CA (US)

( * ) Notice: Subject to any disclaimer, the term of this patent is extended or adjusted under 35 U.S.C. 154(b) by 296 days.

(21) Appl. No.: 15/424,608

(22) Filed: Feb. 3, 2017

(65) Prior Publication Data

US 2017/0215749 A1    Aug. 3, 2017

Related U.S. Application Data

(60) Provisional application No. 62/341,601, filed on May 25, 2016, provisional application No. 62/290,642, filed on Feb. 3, 2016.

(51) Int. Cl.
*A61B 5/00* (2006.01)
*A61B 5/021* (2006.01)
(Continued)

(52) U.S. Cl.
CPC .......... *A61B 5/02141* (2013.01); *A61B 5/002* (2013.01); *A61B 5/02055* (2013.01);
(Continued)

(58) Field of Classification Search
CPC . A61B 5/022; A61B 5/02216; A61B 5/02233; A61B 5/02241; A61B 5/02055;
(Continued)

(56) References Cited

U.S. PATENT DOCUMENTS 4,821,734 A * 4/1989 Koshino ............ A61B 5/02255
600/493
8,430,822 B2 * 4/2013 Inoue ................. A61B 5/02116
600/490
(Continued)

FOREIGN PATENT DOCUMENTS

CN     204765590 U    11/2015
WO     2017/136772 A1    8/2017

OTHER PUBLICATIONS

International Search Report in International Application No. PCT/US2017/016580, dated Apr. 25, 2017.
(Continued)

*Primary Examiner* — Max F Hindenburg
(74) *Attorney, Agent, or Firm* — Schwabe Williamson & Wyatt, PC

(57) ABSTRACT

A blood pressure monitoring device includes a body portion having a size and structure to extend around an appendage of a user during use, a fluid bladder at least one of attached to or integral with the body portion and arranged to be able to apply pressure to an adjacent artery or vein of the user during use, a pressure actuator fluidly connected to the fluid bladder, a controller configured to provide control signals to the pressure actuator to fill the fluid bladder to selected pressures, a signal processor configured to communicate with the controller to receive signals indicating the selected pressures to which the fluid bladder is filled, and a pressure sensor arranged in operative contact with the fluid bladder to measure blood pressure waveforms plus bladder fluid pressure to provide a pressure waveform signal containing information regarding a relationship between vessel distention and transmural pressure. The pressure sensor is further configured to communicate with the signal processor to provide the pressure waveform signal to the signal processor. The controller is configured to provide a plurality of
(Continued)

selected pressures that are less than a mean arterial pressure of the user, and the signal processor is configured to calculate blood pressure parameters using pressure waveform signals produced during application of the plurality of selected pressures that are less than the mean arterial pressure of the user.

14 Claims, 18 Drawing Sheets

(51) Int. Cl.
- A61B 5/0205 (2006.01)
- A61B 5/022 (2006.01)
- A61B 5/026 (2006.01)
- A61B 5/0402 (2006.01)
- A61B 5/053 (2006.01)
- A61B 5/08 (2006.01)

(52) U.S. Cl.
CPC ...... *A61B 5/02116* (2013.01); *A61B 5/02225* (2013.01); *A61B 5/02241* (2013.01); *A61B 5/7278* (2013.01); *A61B 5/0261* (2013.01); *A61B 5/0402* (2013.01); *A61B 5/0533* (2013.01); *A61B 5/0816* (2013.01); *A61B 2560/0214* (2013.01); *A61B 2560/0223* (2013.01)

(58) Field of Classification Search
CPC .............. A61B 5/02116; A61B 5/7278; A61B 5/02141; A61B 5/002; A61B 5/02225
See application file for complete search history.

(56) References Cited

U.S. PATENT DOCUMENTS

| | | | | |
|---|---|---|---|---|
| 8,517,951 | B2* | 8/2013 | Fujii | A61B 5/02125 |
| | | | | 600/490 |
| 8,795,185 | B2* | 8/2014 | Cho | A61B 5/0059 |
| | | | | 600/480 |
| 9,138,161 | B2* | 9/2015 | Lading | A61B 5/02007 |
| 9,662,121 | B2* | 5/2017 | Masaki | A61B 17/135 |
| 9,962,094 | B2* | 5/2018 | Ono | A61B 5/02007 |
| 10,004,409 | B2* | 6/2018 | McCombie | A61B 5/026 |
| 10,016,139 | B2* | 7/2018 | Kinoshita | A61B 5/024 |
| 10,271,751 | B2* | 4/2019 | Muhlsteff | A61B 5/0285 |
| 2006/0229517 | A1 | 10/2006 | Lin et al. | |
| 2009/0156946 | A1 | 6/2009 | Lane et al. | |
| 2011/0245633 | A1 | 10/2011 | Goldberg et al. | |
| 2013/0060152 | A1 | 3/2013 | Baron | |

OTHER PUBLICATIONS

Buxi et al. A survey on signals and systems in ambulatory blood pressure monitoring using pulse transit time. Physiological measurement, 36(3):R1, 2015.

Cameron et al. Use of radial artery applanation tonometry and a generalized transfer function to determine aortic pressure augmentation in subjects with treated hypertension. Journal of the American College of Cardiology, 32(5):1214-1220, 1998.

Chen et al. Assessment of algorithms for oscillometric blood pressure measurement. In Instrumentation and Measurement Technology Conference, 2009. I2MTC'09. IEEE, pp. 1763-1767. IEEE, 2009.

Colak et al. Blood pressure estimation using neural networks. In Computational Intelligence for Measurement Systems and Applications, 2004. CIMSA. 2004 IEEE International Conference on, pp. 21-25. IEEE, 2004.

Forouzanfar et al. Feature-based neural network approach for oscillometric blood pressure estimation. IEEE Transactions on Instrumentation and Measurement, 60(8):2786-2796, 2011.

Geddes et al. Characterization of the oscillometric method for measuring indirect blood pressure. Annals of Biomedical Engineering, 10(6):271-280, 1982.

Gesche et al. Continuous blood pressure measurement by using the pulse transit time: comparison to a cuff-based method. European journal of applied physiology, 112(1):309-315, 2012.

He et al. An ear-worn vital signs monitor. IEEE Transactions on Biomedical Engineering, 62(11):2547-2552, 2015.

He et al. The ear as a location for wearable vital signs monitoring. In 2010 Annual International Conference of the IEEE Engineering in Medicine and Biology, pp. 6389-6392. IEEE, 2010.

Jeon et al. A simulation for estimation of the blood pressure using arterial pressure-volume model. World Academy of Science, Engineering and Technology, International Journal of Medical, Health, Biomedical, Bioengineering and Pharmaceutical Engineering, 1(6):419-424, 2007.

Lim et al. Improved measurement of blood pressure by extraction of characteristic features from the cuff oscillometric waveform. Sensors, 15(6):14142-14161, 2015.

Liu et al. Extraction of an arterial stiffness index from oscillometry. Journal of Medical and Biological Engineering, 27(3):116-123, 2007.

McCarthy et al. An examination of calibration intervals required for accurately tracking blood pressure using pulse transit time algorithms. Journal of human hypertension, 27(12):744-750, 2013.

Meidert et al. Radial artery applanation tonometry for continuous non-invasive arterial pressure monitoring in intensive care unit patients: comparison with invasively assessed radial arterial pressure. British journal of anesthesia, p. aet400, 2013.

Oh et al. The modified step-wise deflation method in blood pressure measurement. In 2008 Computers in Cardiology, pp. 169-172. IEEE, 2008.

Poon et al. The beat-to-beat relationship between pulse transit time and systolic blood pressure. In 2008 International Conference on Information Technology and Applications in Biomedicine, pp. 342-343. IEEE, 2008.

Raamat et al. Comparison of oscillometric pulse amplitude envelopes recorded from the locally compressed radial arteries. Medical engineering & physics, 32(10):1124-1130, 2010.

Raamat et al. Mathematical modelling of non-invasive oscillometric finger mean blood pressure measurement by maximum oscillation criterion. Medical & biological engineering & computing, 37(6):784-788, 1999.

Salvi et al. Validation of a new non-invasive portable tonometer for determining arterial pressure wave and pulse wave velocity: the pulsepen device. Journal of hypertension, 22(12):2285-2293, 2004.

Solà et al. Noninvasive and nonocclusive blood pressure estimation via a chest sensor. IEEE Transactions on Biomedical Engineering, 60(12):3505-3513, 2013.

* cited by examiner

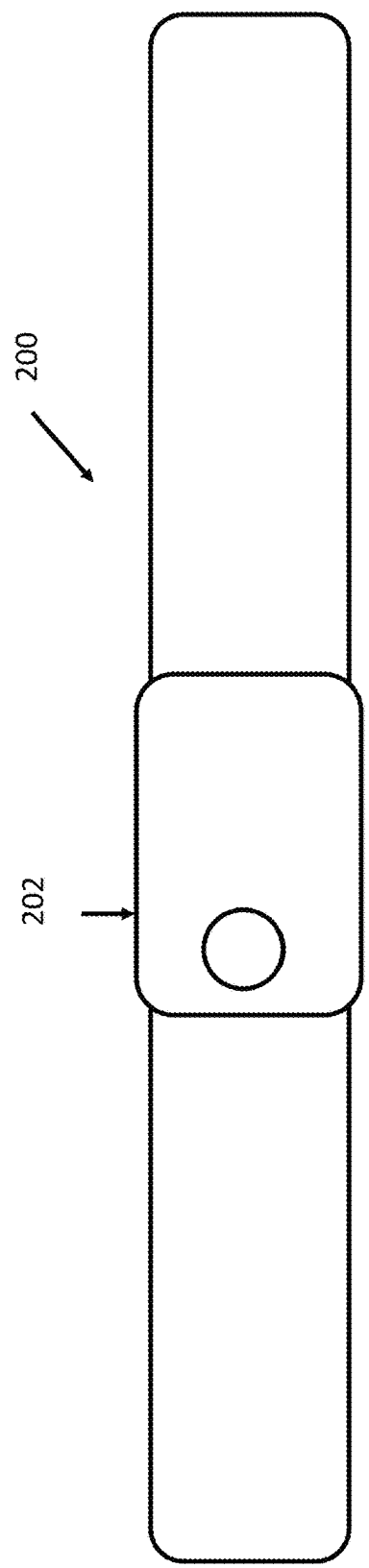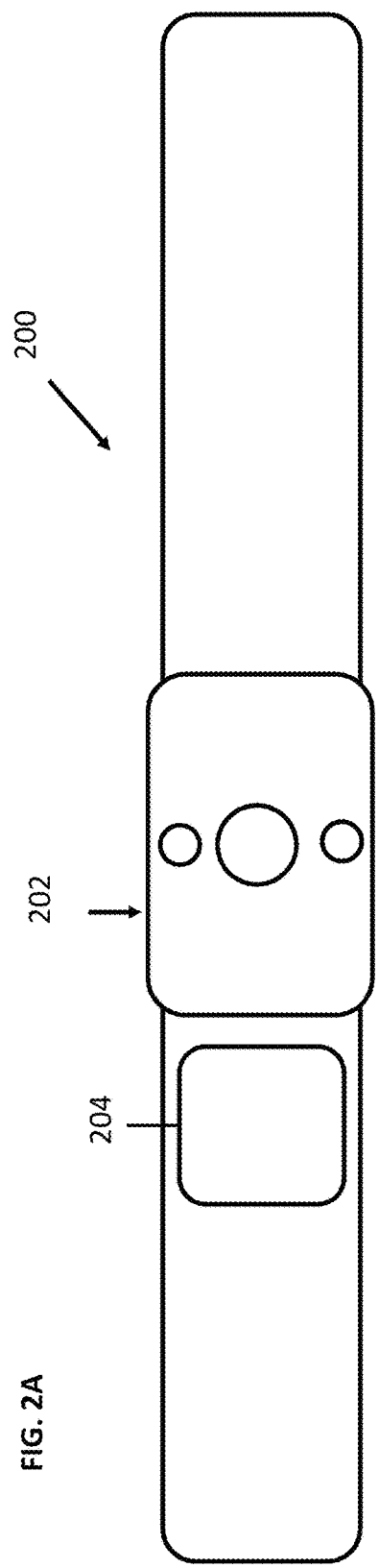
FIG. 2A
FIG. 2B

TABLE 1

| | British Hypertension Society | | | | US Association for the Advancement of Medical Instruments | | | $R^2$ of Model |
|---|---|---|---|---|---|---|---|---|
| | CP 5 | CP 10 | CP 15 | Grade | Mean error | Std error | Compliance | |
| | mmHg | mmHg | mmHg | | | | | |
| Standard | >60% | >85% | >95% | A | <5mmHg | <8mmHg | n/a | n/a |
| Subject 1 | 70% | 100% | 100% | yes | 3.2 mmHg | 3.6 mmHg | yes | 0.88 |
| Subject 2 | 75% | 92% | 100% | yes | 3.0 mmHg | 3.9 mmHg | yes | 0.50 |
| Subject 3 | 77% | 100% | 100% | yes | 0.0 mmHg | 4.5 mmHg | yes | 0.64 |
| Subject 4 | 85% | 100% | 100% | yes | 0.0 mmHg | 3.0 mmHg | yes | 0.75 |
| Subject 5 | 92% | 92% | 100% | yes | 0.0 mmHg | 3.7 mmHg | yes | 0.85 |

FIG. 10

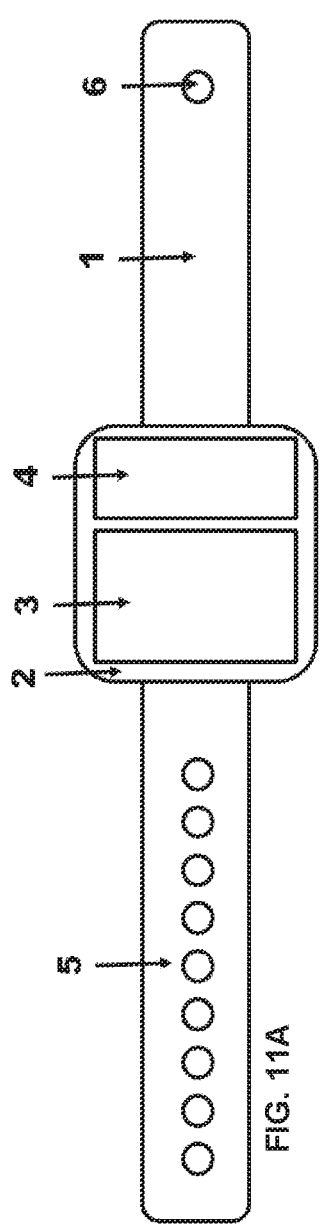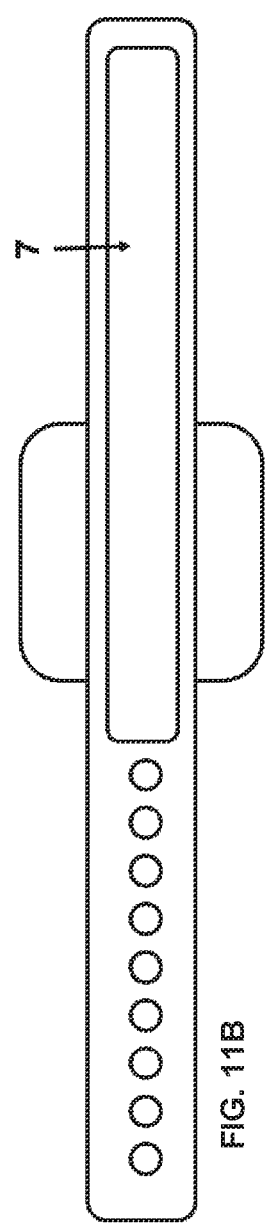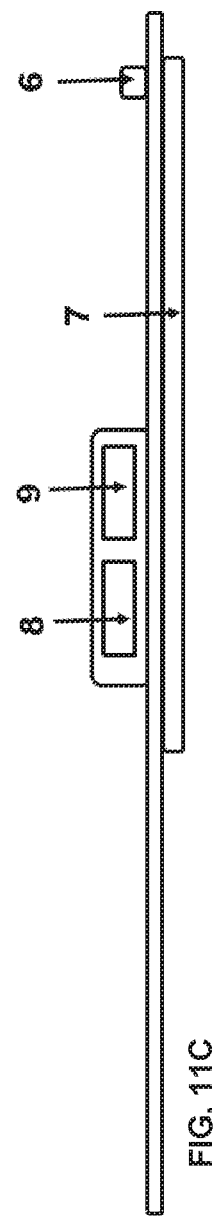
FIG. 11A
FIG. 11B
FIG. 11C

NON-INVASIVE AND NON-OCCLUSIVE BLOOD PRESSURE MONITORING DEVICES AND METHODS

CROSS-REFERENCE OF RELATED APPLICATION

This application claims priority to U.S. Provisional Application No. 62/290,642 filed Feb. 3, 2016, and U.S. Provisional Application No. 62/341,601 filed May 25, 2016, the entire contents of which are hereby incorporated by reference.

BACKGROUND

1. Technical Field

The field of the currently claimed embodiments of this invention relates to blood pressure monitoring devices and methods, and more particularly to non-invasive and non-occlusive blood pressure monitoring devices and methods.

2. Discussion of Related Art

Cuff sphygmomanometer has been the gold standard for measuring blood pressure non-invasively. However, it requires the occlusion of the blood vessel by means of applying external pressure, specifically applying an unloading pressure to above the systolic pressure. Cuffs are bulky and a hassle to take on and off, and when inflated, inhibit return of venous blood to the heart and lungs. As a result, users have to stand the inconvenience and discomfort or even pain to take blood pressure measurements. These limitations of the Riva-Rocci cuff sphygmomanometer makes it unsuitable for highly frequent blood pressure monitoring.

The method used by most of the current automatic blood pressure monitors is the oscillometric waveform method, developed from cuff sphygmomanometer. It analyzes the cuff oscillation amplitudes generated by recording the cuff pressures in the process of applying an external pressure to the artery that goes above the systolic pressure and gradually bleeds down to below the diastolic pressure, and defines the systolic point at about 50% of the peak height on the rising phase of the envelope, and the diastolic point at 70% of the peak height on the falling phase of the envelope. (Baker P D, Westenskow D R, Kuck K: Theoretical analysis of non-invasive oscillometric maximum amplitude algorithm for estimating mean blood pressure. Med Biol Eng Comput 1997, 35: 271-278.) The need for high unloading pressure makes it challenging to design a low power blood pressure monitor with miniaturized components, as well as being comfortable enough to wear for repeated measurements. Thus, the current way of monitoring blood pressure still remains largely on single or very few point measurements at the clinic or at home.

Further, studies have shown that factors such as artery stiffness, cuff sizes, or arm circumferences have great impact on the accuracy of the oscillometric method. (van Popele N M, Bos W J W, de Beer N A M, van der Kuip D A M, Hofman A, Grobbee D E, Witteman J C M: Arterial stiffness as underlying mechanism of disagreement between an oscillometric blood pressure monitor and a sphygmomanometer. Hypertension 2000, 36: 484-488; Stork M, Jilek J: Cuff pressure waveforms: their current and prospective application in biomedical instrumentation. In Biomedical Engineering Trends in Electronics, Communications and Software. Edited by: Laskovski A N. InTech; 2011:193-210; Bur Al, Hirschl M M, Herkner H, Oschatz E, Kofler J, Woisetschläger C, Laggner A N: Accuracy of oscillometric blood pressure measurement according to the relation between cuff size and upper-arm circumference in critically ill patients. Crit Care Med 2000, 28(2):371-6.) A lot of clinicians question the accuracy of the automatic blood pressure monitors patients bought from pharmacies and request the patients to bring them to the clinics for calibration.

Therefore, there is unmet need for providing methods and apparatuses for comfortable, wearable, and accurate blood pressure monitoring.

SUMMARY

A blood pressure monitoring device according to some embodiments of the current invention includes a body portion having a size and structure to extend around an appendage of a user during use, a fluid bladder at least one of attached to or integral with the body portion and arranged to be able to apply pressure to an adjacent artery or vein of the user during use, a pressure actuator fluidly connected to the fluid bladder, a controller configured to provide control signals to the pressure actuator to fill the fluid bladder to selected pressures, a signal processor configured to communicate with the controller to receive signals indicating the selected pressures to which the fluid bladder is filled, and a pressure sensor arranged in operative contact with the fluid bladder to measure blood pressure waveforms plus bladder fluid pressure to provide a pressure waveform signal containing information regarding a relationship between vessel distention and transmural pressure. The pressure sensor is further configured to communicate with the signal processor to provide the pressure waveform signal to the signal processor. The controller is configured to provide a plurality of selected pressures that are less than a mean arterial pressure of the user, and the signal processor is configured to calculate blood pressure parameters using pressure waveform signals produced during application of the plurality of selected pressures that are less than the mean arterial pressure of the user.

A method of monitoring blood pressure according to some embodiments of the current invention includes applying at least one of a plurality of pressures or a time-varying pressure to a position of an artery or a vein of a subject, measuring pressure during the applying at least one of a plurality of pressures or a time-varying pressure to provide data signals for combined applied and oscillatory pressure waveforms during the applying, calculating blood pressure parameters from the data signals, and at least one of displaying, transmitting or storing the blood pressure parameters. The at least one of the plurality of pressures or the time-varying pressure are less than a mean arterial blood pressure of the subject.

BRIEF DESCRIPTION OF THE DRAWINGS

Further objectives and advantages will become apparent from a consideration of the description, drawings, and examples.

FIGS. 2A and 2B show top and bottom views, respectively, of a blood pressure monitoring device according to another embodiment of the current invention.

FIG. 7A shows data obtained under rest condition, 7B is a plot of data points obtained after upper body exercise that extensively dilated the blood vessel in the arms, and 7C is plotted from measurements obtained after lower body exercise, which leads to vasoconstriction of the arteries of the arms. Each of the conditions were measured at 4 different relative vertical positions of the fluid bladder on the arm, to the heart: 1) heart level, 2) arms naturally hanging down at the sides of the body, 3) arm raised 10 cm higher than heart level, and 4) arm raised 20 cm higher than heart level. Data points are obtained from the brachial artery.

FIG. 10 is Table 1 which provides results of the fit of plane model in 5 subjects compared to standards of British Hypertension Society and US Association for the Advancement of Medical Instruments, and the $R^2$ of the fit of the plan models.

FIGS. 11A-C show a schematic illustration of top, bottom, and side views, respectively, of a blood pressure monitoring device according to an embodiment of the current invention.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Figure 1:
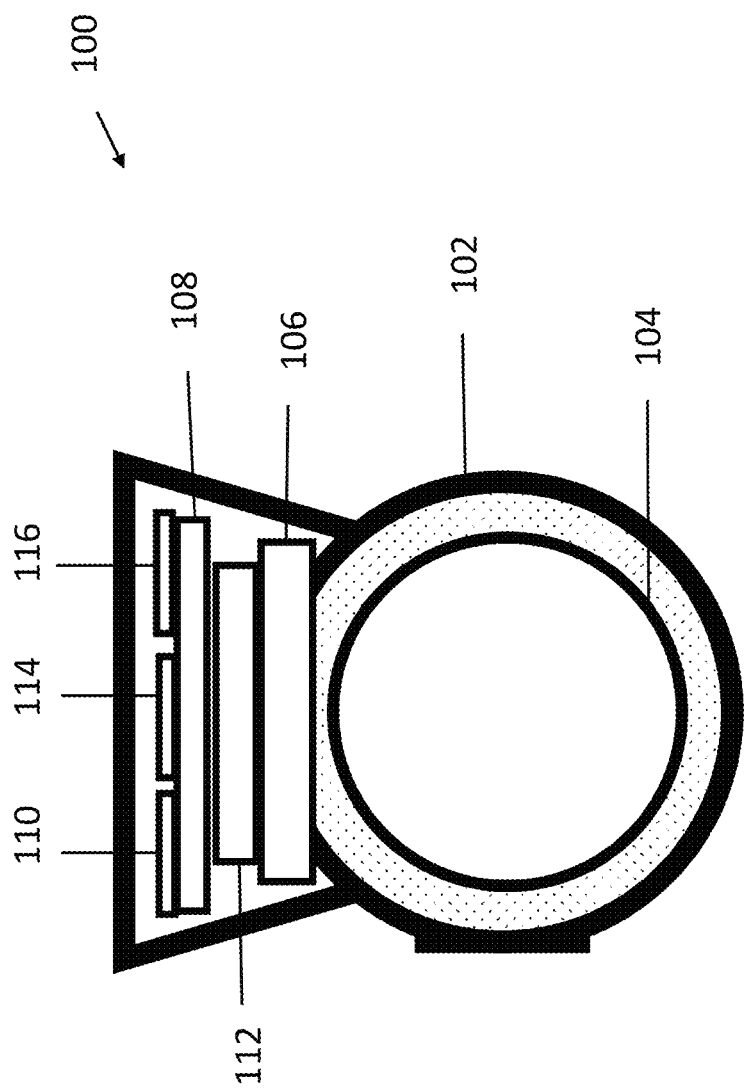
FIG. 1 is a schematic illustration of a blood pressure monitoring device according to an embodiment of the current invention.

FIG. 1 is a schematic illustration of a blood pressure monitoring device 100 according to an embodiment of the current invention. The blood pressure monitoring device 100 includes a body portion 102 having a size and structure to extend around an appendage of a user during use, a fluid bladder 104 at least one of attached to or integral with the body portion 102 and arranged to be able to apply pressure to an adjacent artery or vein of the user during use, and a pressure actuator 106 fluidly connected to the fluid bladder 104. The blood pressure monitoring device 100 is illustrated in the form of a ring to be worn on a finger or toe of the user in this embodiment. However, the general concepts of the current invention are not limited to this embodiment. Other embodiments, as will be shown in particular examples below, can be in the form of a wrist or ankle band, or an arm or leg strap similar to forms of conventional blood pressure devices. These are intended to be non-limiting examples since one could also envision structures that clamp onto the user, for example.

The fluid bladder 104 and pump 106 can be constructed for any suitable fluid, such as, but not limited to a liquid and/or a gas. For example, the fluid can be air in some embodiments, but the general concepts of the current invention are not limited to this example.

The embodiment illustrated in FIG. 1 has an integrated circuit 108 that can include a controller configured to provide control signals to the pressure actuator 106 to fill the fluid bladder 104 to selected pressures. The integrated circuit 108 can also include a signal processor configured to communicate with the controller to receive signals indicating the selected pressures to which the fluid bladder 104 is filled. Although this embodiment illustrates an integrated circuit 108 that includes the controller and signal processor, the general concepts of the current invention are not limited to this particular example. For example, the signal processor and controller could be separate components and arranged differently from the example of FIG. 1. In some embodiments, the signal processor could be partially or wholly exterior to the body portion 102 such that some or all of the signal processing can be performed external to the structure that is worn by the user. For example, some embodiments can include a wireless transmitter included in the integrated circuit 108 to transmit raw unprocessed signals and/or partially processed signals, or even completely processed signals. Although wireless transmission is advantageous for many applications, other embodiment could include hard-wired transmission of the raw, partially processed and/or completely processed signals. The term wireless can include any transmission mode such as radio frequency, infrared and/or optical transmission, for example. The blood pressure monitoring device 100 also includes a pressure sensor 110 arranged in operative contact with the fluid bladder 104 to measure pressure waveforms of pulse oscillation plus bladder fluid pressure to provide a pressure waveform signal containing information regarding a relationship of vessel distention and transmural pressure. The pressure sensor 110 is also configured to communicate with the signal processor (on integrated circuit 108 in this example) to provide the pressure waveform signal to the signal processor.

The controller (on integrated circuit 108 in this example) is configured to provide a plurality of selected pressures that are less than a mean arterial pressure of the user, and the signal processor is configured to calculate systolic and diastolic blood pressures using pressure waveform signals produced during application of the plurality of selected pressures that are less than the mean arterial pressure of the user.

In some embodiments, the controller is configured to provide the plurality of selected pressures such that all selected pressures are less than a diastolic blood pressure of the user. In some embodiments, the pump controller is configured to provide only selected pressures that are less than the diastolic blood pressure of the user. In some embodiments, the pump controller is configured to provide only selected pressures that are at least 20 mmHg and less than 40 mmHg.

In some embodiments, the blood pressure monitoring device 100 can also include an energy storage component 112 that can be charged and supply power to the blood pressure monitoring device 100. For example, the energy storage device can include one or more batteries, capacitors and/or supercapacitors, for example.

In some embodiments, the signal processor is configured to use a model in conjunction with the pressure waveform signals produced during the plurality of selected pressures to calculate the systolic and diastolic blood pressures. In some embodiments, the model is at least one of a pre-determined subject-specific model, a demographic-specific model, a generalized model based on large scale population study, or a self-calibration model.

In some embodiments, the blood pressure monitoring device 100 can also include at least one of an accelerometer or a gyroscope 114 at least one of attached to, contained within or integral with the body portion 102. At least one of the accelerometer or the gyroscope can be further configured to communicate with the signal processor such that the signal processor can utilize at least one of motion, position or orientation information of the user for calculating the systolic and diastolic blood pressures and interpreting data.

In some embodiments, the blood pressure monitoring device 100 can also include additional sensors 116 which can be, but is not limited to at least one of an electrocardiography (ECG) sensor and a photoplethysmography (PPG) sensor, or two PPG sensors at least one of attached to, contained within or integral with the body portion 102 such that the additional sensors 116 are in communication with the signal processor. The signal processor can be further configured to extract information of blood flow propagation along the arterial tree to be used in conjunction with information from the pressure waveform signals to calculate the systolic and diastolic blood pressures.

FIGS. 2A and 2B show top and bottom views, respectively, of a blood pressure monitoring device 200 according to another embodiment of the current invention. The blood pressure monitoring device 200 includes a body portion 202 having a size and structure to extend around an appendage of a user during use, a fluid bladder 204 at least one of attached to or integral with the body portion 202 and arranged to be able to apply pressure to an adjacent artery or vein of the user during use, and a pressure actuator (not visible in FIGS. 2A and 2B) fluidly connected to the fluid bladder 204. The blood pressure monitoring device 200 is illustrated in the form of a wrist band to be worn on a wrist or ankle of the user in this embodiment. However, this configuration can also be directly adapted to wrap around the user's arm or leg for example. Additional features and components of an embodiment of a wrist band will be shown in more detail below in the examples.

EXAMPLES

The following examples help explain some concepts of the current invention. However, the general concepts of the current invention are not limited to the particular examples.

1. Continuous Non-Invasive, Non-Occlusive Blood Pressure Measurement Using Subject-Specific and Demographic-Specific Pulse Pressure Models This embodiment of the current invention is directed to methods and apparatuses for continuous, non-invasive, and non-occlusive measurement of blood pressure using subject-specific models. In particular, it relates to methods of measuring blood pressure through analyzing pulse pressure under various conditions of mechanical unloading of the vessel wall, and building mathematical and statistical models to characterize cardiovascular parameters under conditions of different vascular tone, so that accurate blood pressure measurements can be obtained. In some embodiments, subject-specific and demographic-specific models are used to decouple the cardiovascular parameters and predict blood pressure.

We use the term "demographic" to refer not only to ethnicity, gender and age, but also to population subgroups differentiated by body size, weight, and health status.

We use the term "continuous" to refer to an ability to obtain frequent estimates of cardiovascular parameters from an individual under conditions where adequate measurements are available to produce estimates. The maximum frequency of such measurements is achieved when an estimate is produced for each heartbeat.

Related Art

Accurate monitoring of blood pressure (BP) in a continuous, non-invasive way has proven a challenging task. Most attempts at continuous measurement are based on transit time of the blood pressure pulse (pulse transit time [PTT]) and exploit the fact that PTT is generally inversely correlated with blood pressure. These methods are not accurate because many factors other than blood pressure affect pulse arrival time. For example, a dose of sublingual nitroglycerin (NG) has a strong relaxing effect on the arterial system, leading to large increases in PTT. (J. S. Maltz and T. F. Budinger, "Evaluation of arterial endothelial function using transit times of artificially induced pulses," Physiological Measurement, vol. 26, no. 3, pp. 293-307, 2005. [Online]. Available: http://stacks.iop.org/0967-3334/26/293.) However, since NG also increases systemic vascular resistance (SVR), the blood pressure is appreciably maintained. (J. Gisolf, B. E. Westerhof, N. van Dijk, K. H. Wesseling, W. Wieling, and J. M. Karemaker, "Sublingual nitroglycerin used in routine tilt testing provokes a cardiac output-mediated vasovagal response," Journal of the American College of Cardiology, vol. 44, no. 3, pp. 588-593, 2004. [Online]. Available: http://www.sciencedirect.com/science/article/pii/S0735109704009519.)

Another attempt for measuring continuous, non-invasive blood pressure is tonometry, which tunes external pressure until the pulse amplitude reaches maximum (when transmural pressure is zero) and directly measures the mean arterial pressure (U.S. Pat. No. 6,176,831 B1). It is very sensitive to motion and placement of the sensor, and tone effects and different amounts of fat on the wrist will also affect the reading. Further, because the external pressure needs to reach the mean arterial pressure all the time, red marks will be left after a couple of hours of use, indicating the restriction of blood flow and the unsuitability for prolonged use.

The Riva-Rocci cuff sphygmomanometer produces relatively accurate non-invasive blood pressure measurements, but requires the occlusion of blood by means of application of external pressure. Cuffs are bulky and even when inflated to low pressures, inhibit return of venous blood to the heart and lungs. This is uncomfortable for the user, inconvenient to use in ambulatory monitoring, and are thus not ideal for continuous measurement. Continuous use would result in injury to the subject and inaccurate readings.

Therefore, a need exists for providing methods and apparatuses to measure blood pressure continuously (or at higher frequency than practicable using Riva-Rocci sphygmomanometers), in a non-invasive and non-occlusive way, and to address the confounding effects of vascular tone on blood pressure calculation.

Accordingly, an aspect of this embodiment of the current invention is to provide methods for continuous non-invasive blood pressure monitoring using non-occlusive, pulse pressure analysis. Another aspect of this embodiment is to provide calibration methods for constructing subject-specific or demographic-specific models. Another aspect of this embodiment is to provide apparatuses for taking pulse pressure measurements that can be analyzed for blood pressure, as well as other information to assist with the interpretation of blood pressure.

In accordance with the first aspect of this invention, there are provided methods to measure BP by first collecting the waveforms of pulse pressure while different external pressures are exerted on the artery. Typically, these externally applied pressures are below the mean arterial pressure. Models are fit to the waveforms, which can produce blood pressure estimates. This invention teaches the utility of measuring blood pressure by means of the exploitation of the linear (or approximately linear, or monotonic) relationship between transmural pressure (TMP, pressure difference between the lumen of the artery and the exterior of the wall of the same artery) and the logarithm of the amplitude of the pulse pressure change per beat. Equivalently, this may be expressed as the linear (approximately linear, or simply monotonic) relationship between unloading measurement pressure (MP) with the logarithm of amplitude. These relationships allow fitting of models for each of the measurements or combinations of measurements, and the use of the fitted parameters to predict blood pressure (BP) through a mathematical surface/manifold model. In particular, a multivariate linear regression model can be used to fit the coefficients of the linear relationship between TMP or MP and the logarithm of amplitude into a plane surface to predict BP.

According to an embodiment of the current invention, a model fit may be obtained for an individual that, unlike many other indirect methods for estimating BP, is largely independent of other state parameters of the cardiovascular system, including vascular tone. In cases where one set of model parameters is not sufficient to allow accurate estimating of BP in an individual, models can be calibrated to one or more states of the cardiovascular system. Models may be selected for estimation of current BP by detecting the currently prevailing state. Also, by obtaining calibration data for several different states (e.g., post-exercise, after administration of medication), a sufficiently general model or set of models may be fitted in order to more accurately estimate BP in that individual.

Another embodiment of the current invention provides methods to measure a subject's circulatory system parameters under different controlled perturbations so as to collect different operating points of the cardiovascular system to build personalized calibration models with the models described above.

Another embodiment of the current invention provides an apparatus to measure blood pressure by acquiring pulse pressure waveforms using a pressure pump, a pressure sensor, and a pressurized band wrapped around the limb or appendage containing the artery. In some embodiments, the apparatus includes the use of an accelerometer and gyroscope to infer the activity of the user, so that blood pressure measurements can be better interpreted with respect to context.

In some embodiments, the user (individual for whom the measurement is taken) may be alerted and asked questions by a device in order to determine the context of, or reason for a particular measurement, especially when a change in the measurement is not explicable in terms of otherwise monitored parameters.

Figure 2C:
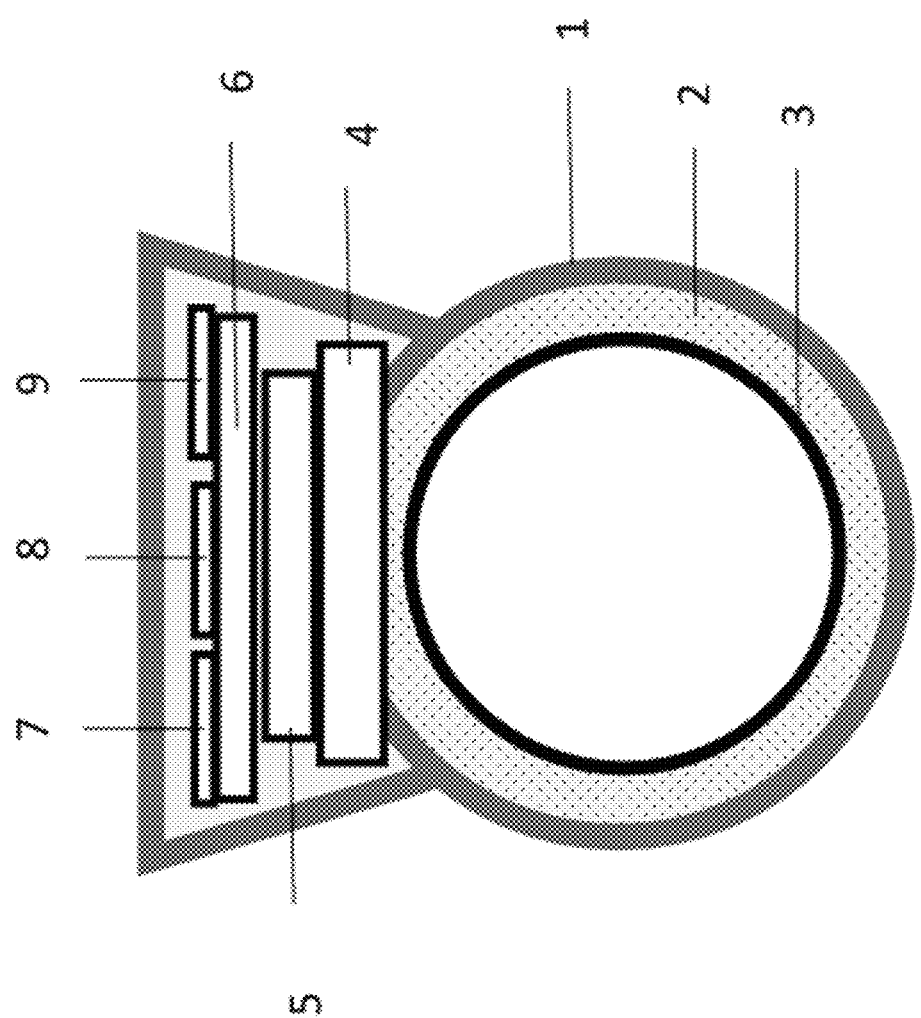
FIG. 2C is a schematic illustration of a blood pressure monitoring device according to an embodiment of the current invention.
Figure 3:
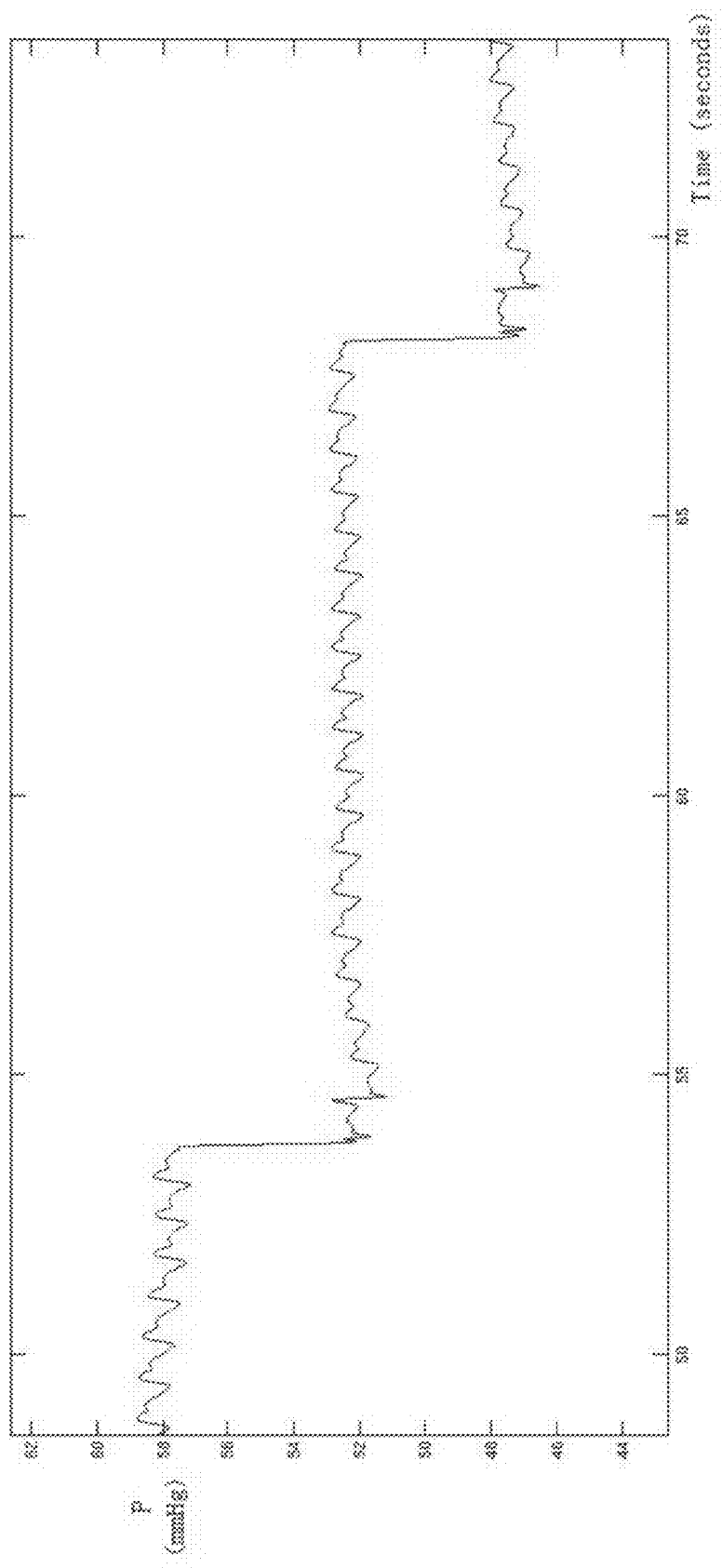
FIG. 3 is an illustration of acquired pulse pressures at three different values of external applied pressure. The waveforms at different external pressures are recorded and analyzed for their characteristics, of which pulse amplitude (height of the rising edge of each pulse) is the most important. The pulses shown here represent the pressure in a fluid bladder. Pressure changes relative to a mean applied pressure value represent displacements induced by changes in blood volume within the artery. These blood volume changes are proportional to the distension of the vessel wall, or vessel distensibility.
Figure 4A:
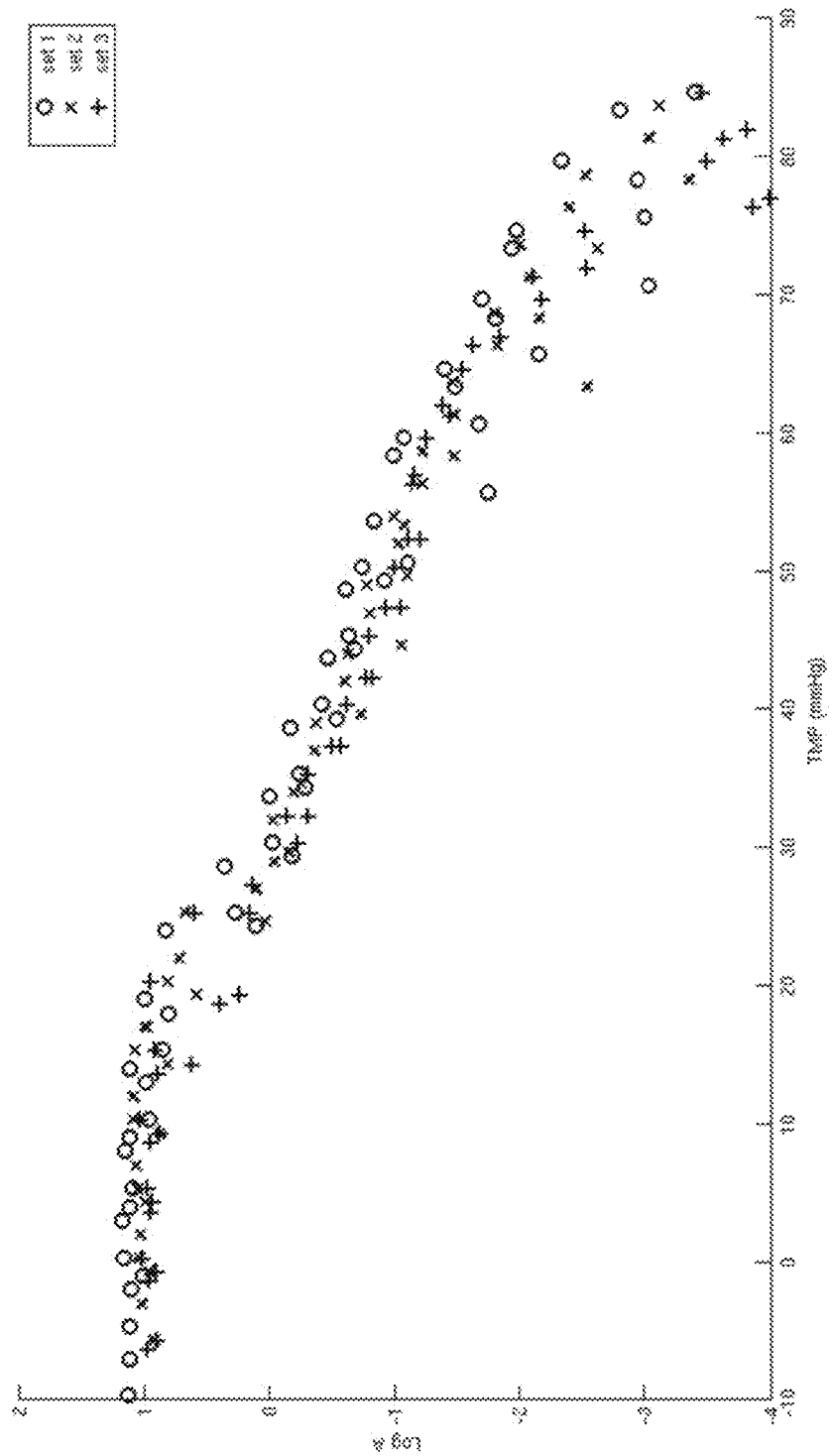
FIGS. 4A and 4B show relationships between log A and TMP (a) and Log A and MP (b). The data are from 3 parallel measurements across a pressure range of 5 mmHg to 90 mmHg. An approximately linear relationship between log A and TMP (and MP) is observed in the range of 15 mmHg to 75 mmHg.
Figure 4B:
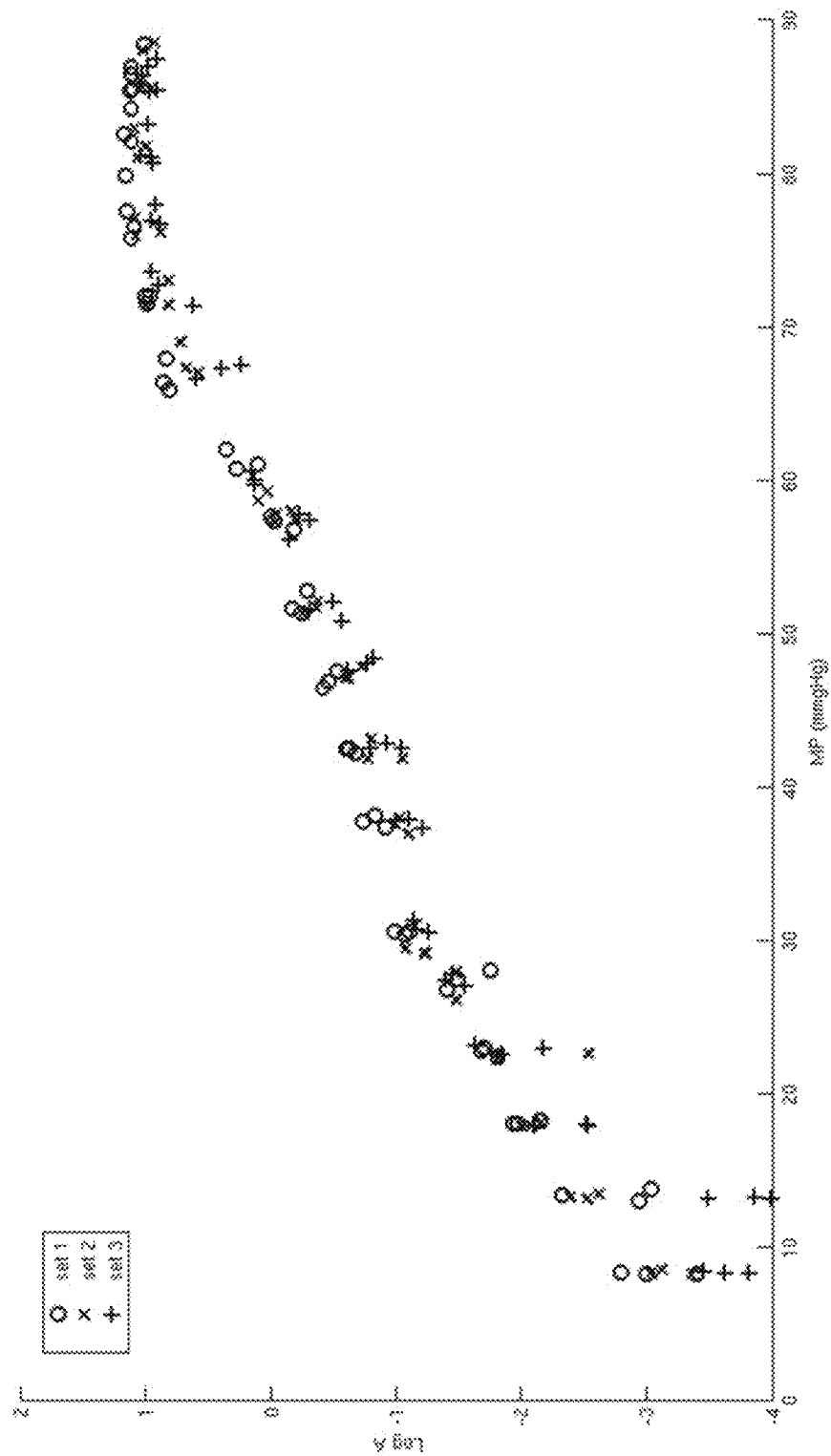
Figure 5:
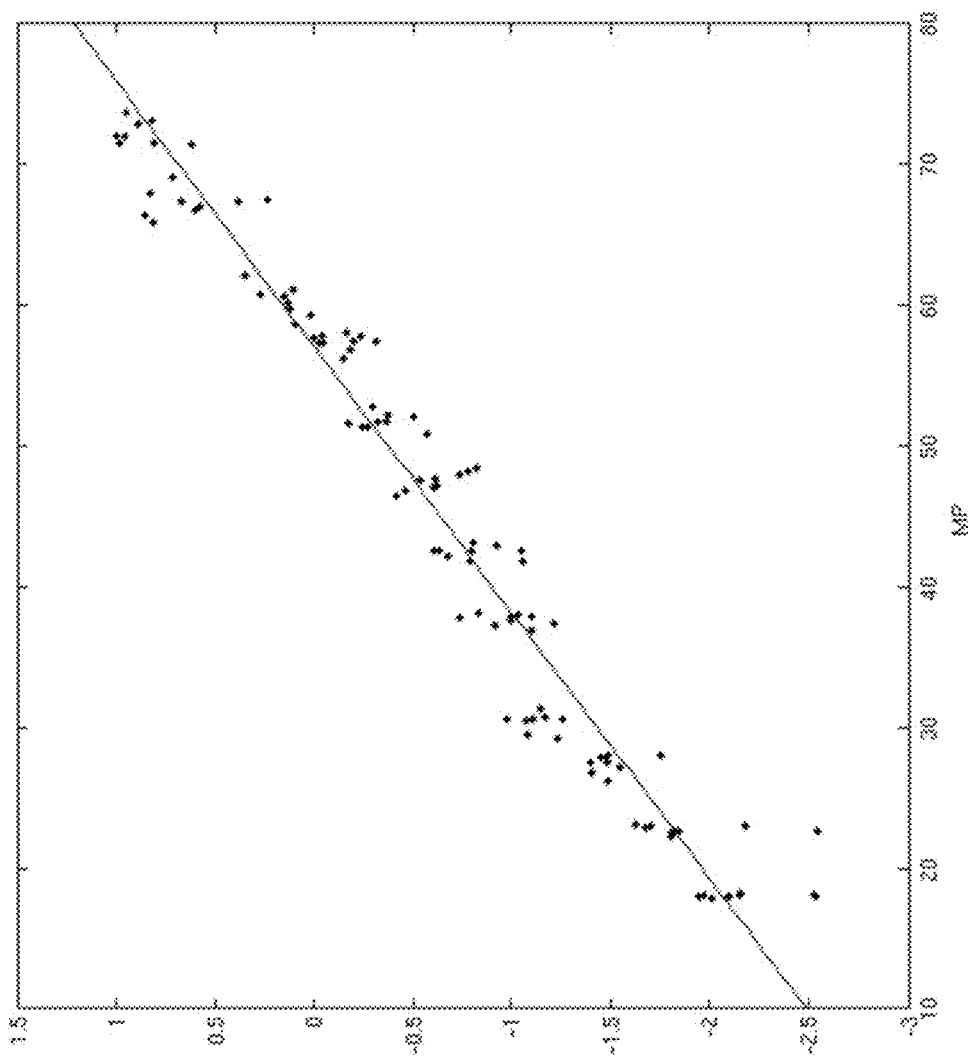
FIG. 5 shows an example of the linear relationship observed between the logarithm of the pulse pressure amplitude (log A) and the external measurement pressure (MP) applied by the fluid bladder. The $R^2$ of the linear fit in these data set is 0.95. The data points in this graph are obtained by capturing pulse pressures while applying external unloading pressures of between 15 mmHg and 75 mmHg. From this linear relationship, we can obtain the coefficients (a',b') by acquiring several time series (two or more) of MP vs log A measurements. Each time series contains one or more pulses.
Figure 6:
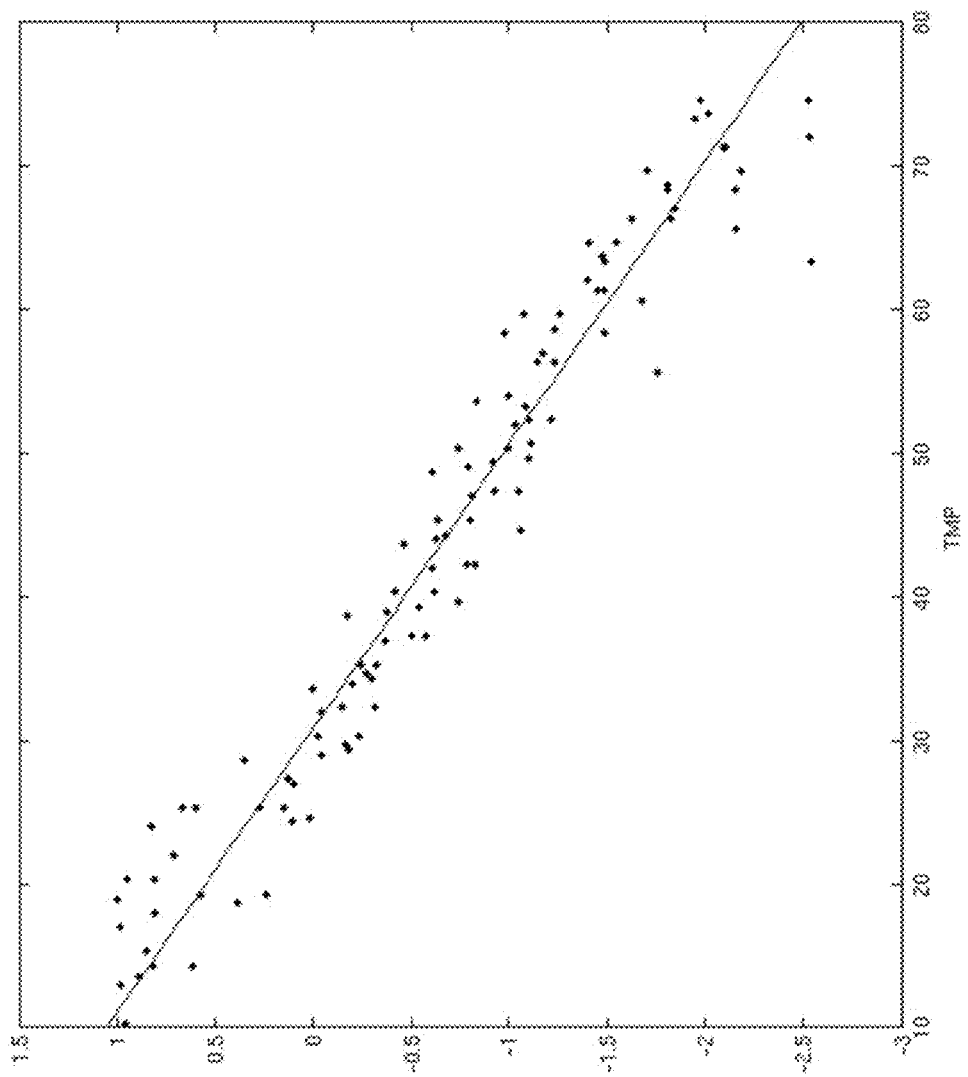
FIG. 6 shows an example of the linear relationship observed between the logarithm of the pulse pressure amplitude (log A) and the transmural pressure (TMP). The $R^2$ of the linear fit in these data set is 0.94. The data points in this graph are obtained by capturing pulse pressures while applying external unloading pressures of between 15 mmHg and 75 mmHg. This linear relationship can be established by acquiring several time series (two or more) of TMP vs log A measurements for understanding the relationship between BP with log A. Each time series contains one or more pulses.
Figure 7A:
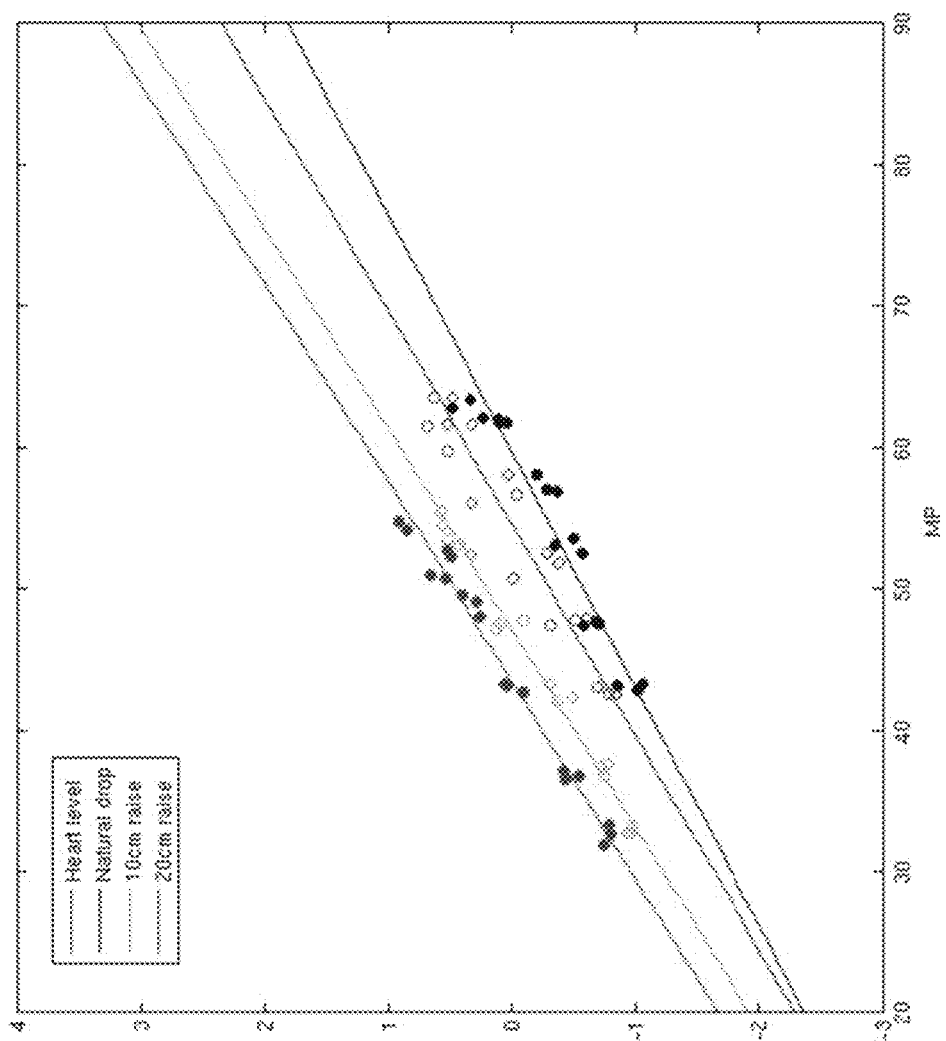
FIGS. 7A-7C show that the linear relationship of MP or TMP with log A is a universal trend.
Figure 7B:
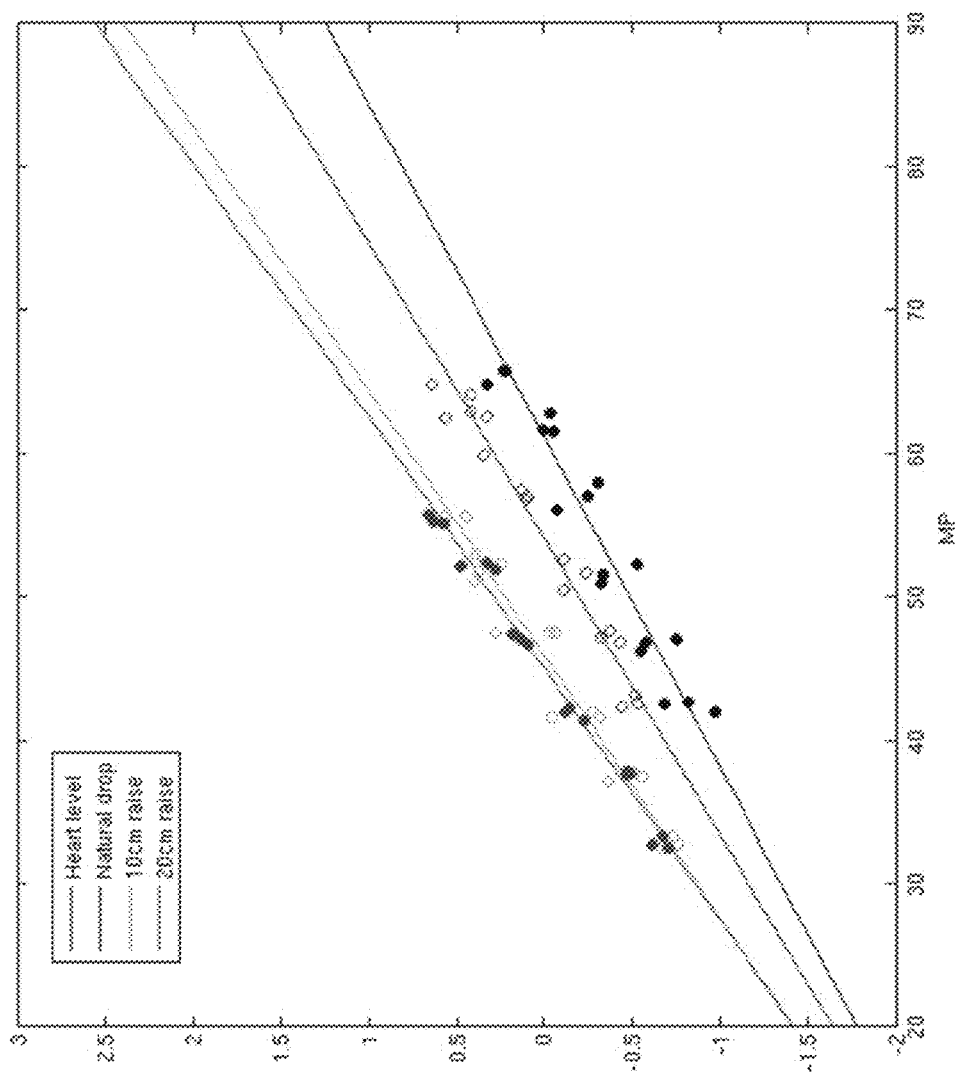
Figure 7C:
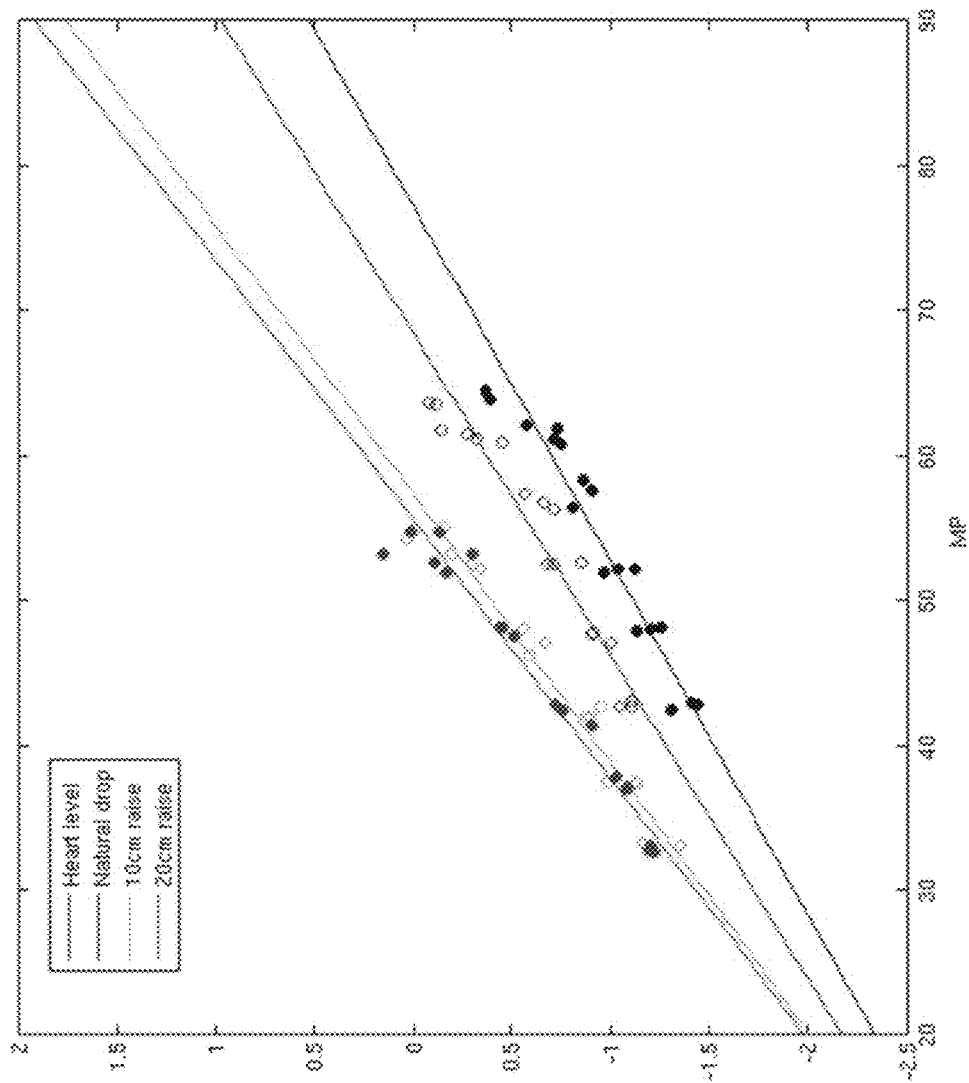
Figure 8:
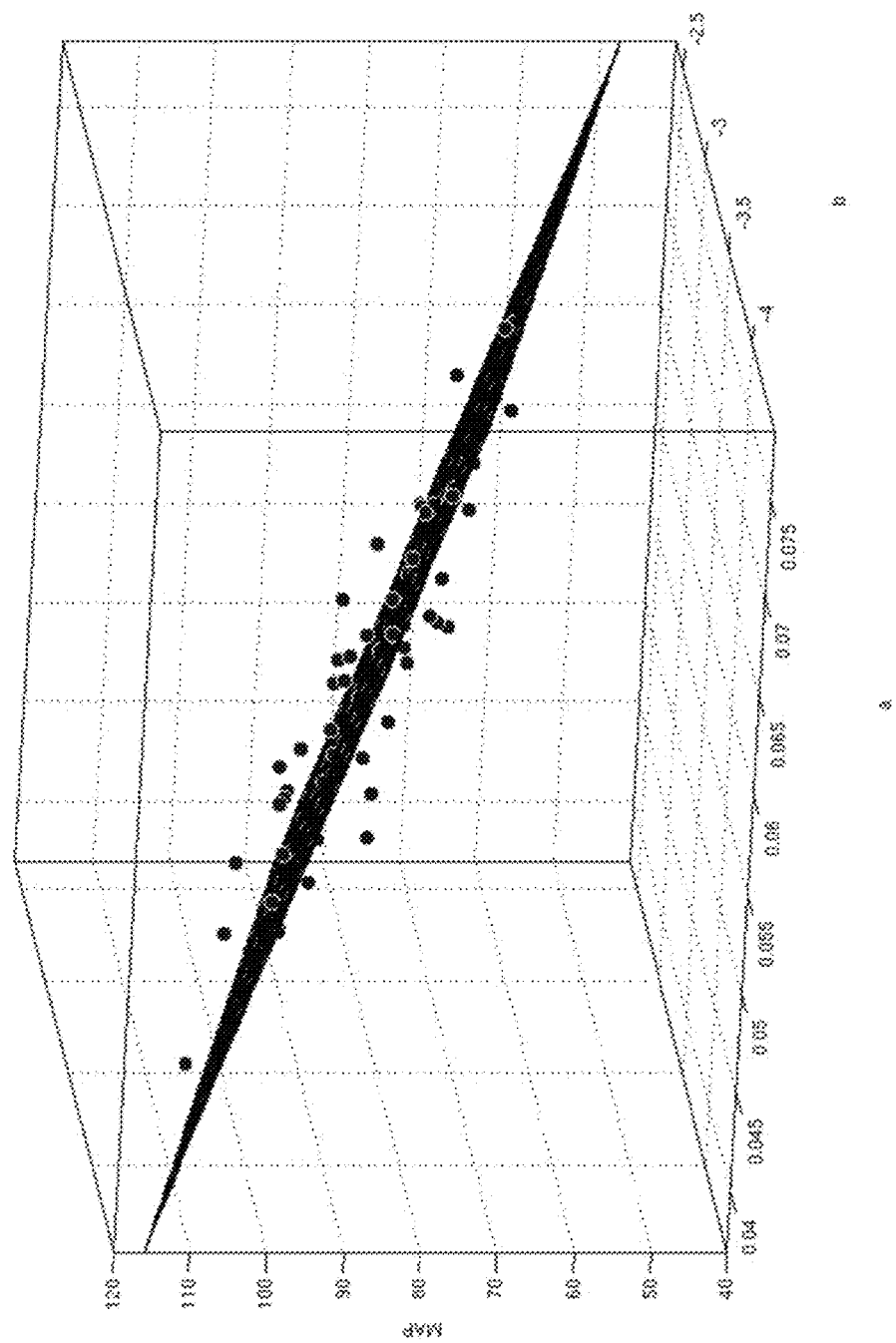
FIG. 8 is an illustration of how effectively a plane can be used to approximate the relationship between mean arterial blood pressure (MAP), the quantity we wish to measure, and the parameters a' and b', which are derived from the measured data (pulse amplitudes as a function of measurement pressure). These measurements are acquired in a single individual under different conditions of vascular tone and states of the cardiovascular system over a time span of 2 weeks: rest, upper body exercises to naturally dilate the artery in the arms, and lower body exercises to naturally constrict the artery in the arms. For each of the conditions, four relative positions to the heart are examined: heart level, natural drop of the arms, 10 cm raise higher than heart level, and 20 cm raise higher than heart level. The $r^2$ of this linear regression analysis is 0.88. The main benefit of the plane model is that theoretically we only need three sets of measurements of (BP, a', b') in order to identify the plane. Further, using this model, and for a given set of (a',b') obtained from fitting MP with log A with at least two sets of MP and log A, we can calculate BP (as MAP) accurately. The fact that a function as simple as a plane can provide this mapping in an individual (over a wide range of arterial tones), is a novel teaching.
Figure 9:
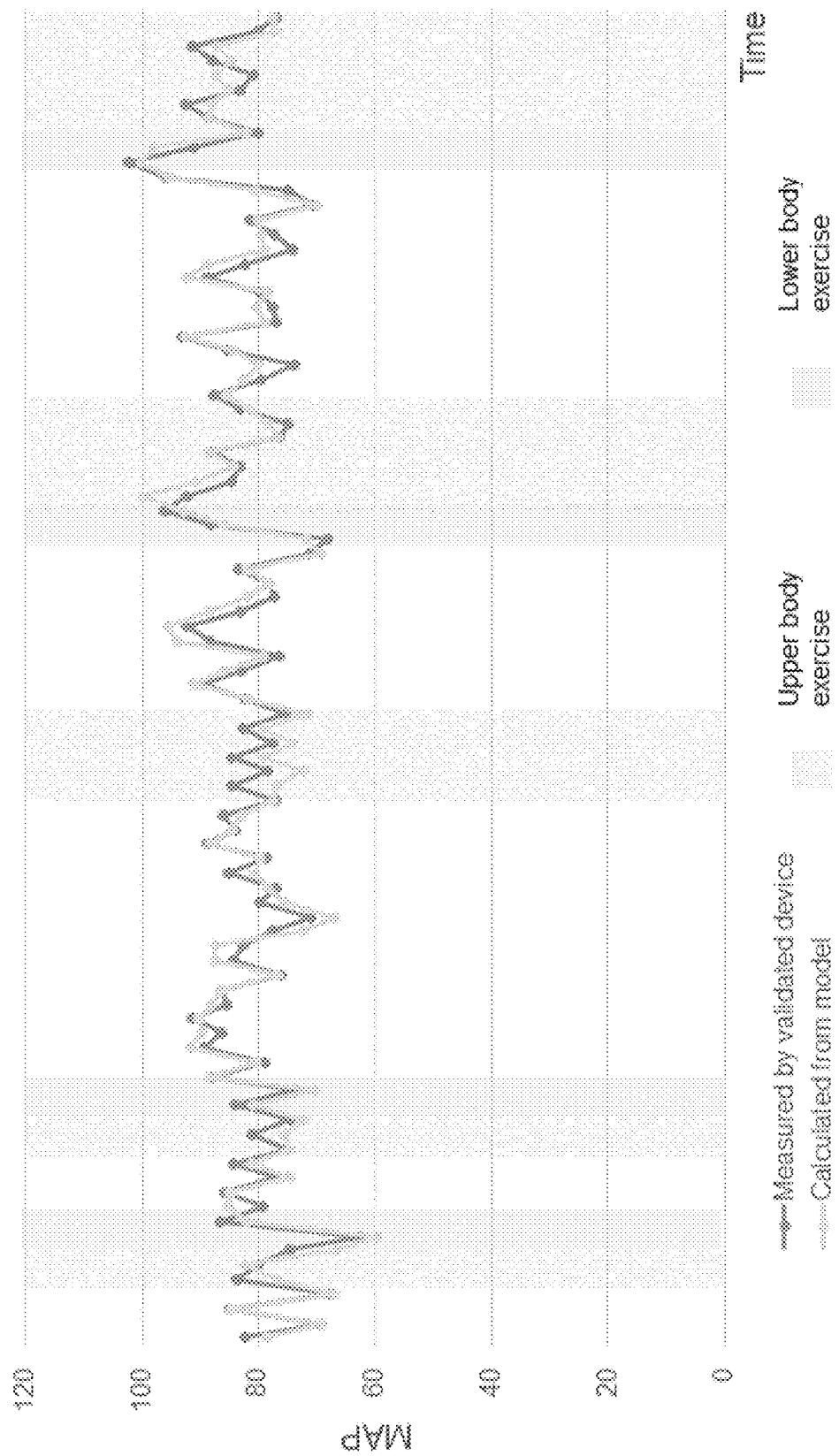
FIG. 9 is an illustration of the robustness and high accuracy achieved by applying the plane model of (MAP, a',b') to calculate blood pressure. The dark grey line is blood pressure measured using a validated Riva-Rocci cuff sphygmomanometer, while the light grey line represents blood pressure calculated from a cross-validation model (half of the data is used to construct a model and the other half is used to calculate blood pressure from the constructed model). These measurements are acquired in a single individual under different conditions of vascular tone and states of the cardiovascular system over a time span of 2 weeks: rest, upper body exercises to naturally dilate the arteries in the arms, and lower body exercises to naturally constrict the arteries in the arms. For each of the conditions, four relative vertical positions of the fluid bladder relative to the heart are examined: heart level, natural drop of the arms, 10 cm raise higher than heart level, and 20 cm raise higher than heart level. The plane model eliminates the confounding factor of vascular tone.

FIG. 2C is an embodiment of an apparatus for continuous/frequent non-occlusive blood pressure measurement based on pulse pressure analysis. It is fabricated as a finger ring, using miniaturized components. 1 is the shell of the ring, which can be made of plastic, metal or other durable and water-proof material. 2 is a space filled with fluid that is controlled by the piezoelectric pump 4, or a vacuum space if pump 4 is an air pump. 3 is a rubber band or other biocompatible fabric that applies external pressure around the arteries. 5 is the battery and charger. 6 is an integrated circuit with Bluetooth connectivity, and sensors such as pressure sensor 7, accelerator/gyroscope 8, and other additional sensors 9. The orders of 4-9 relative to the ring can be switched according to the specific design of the ring, and the sizes of each component can be adjusted.

DETAILED DESCRIPTION

Note that for a given state of arterial tone, an artery follows a very specific characteristic relating transmural pressure (pressure across the arterial wall), to the distensibility of that vessel. By applying two or more distinct external pressures, it is possible to determine the blood pressure by inference, since the transmural pressure (TMP) is equal to the blood pressure minus the applied external pressure. Typically, the tone (elastic state) of the artery is unknown. According to an embodiment of this invention, there is an appreciably predictable (and mathematically expressible) relationship between the distention versus TMP characteristic as a function of different applied pressures, which allows for blood pressure to be inferred appreciably independently of arterial tone.

This ability and novel means of decoupling blood pressure and tone is not exploited by previous methods that seek to use PTT as correlating surrogate for blood pressure. However, given the ability to measure PTT in a vessel segment, via a method such as taught in U.S. Pat. No. 8,666,472, application of external pressure during the measurement of PTT would facilitate such decoupling.

Several properties of human arteries have been characterized as a function of TMP (A. Bank, D. Kaiser, S. Rajala and A. Cheng, "In vivo human brachial artery elastic mechanics: Effects of smooth muscle relaxation," *Circulation*, vol. 100, pp. 41-7, 1999.), but these characteristics have not been used previously to measure or estimate blood pressure. In particular, the beat-by-beat peak artery distention has not apparently been characterized as a function of TMP in the range below diastolic pressure, and has not been used to measure or estimate blood pressure.

Analysis of Pulse Pressure Waveforms

Another embodiment of the current invention provides methods to measure BP by analyzing pulse pressures generated during intervals in which variable pressure is applied around one or more arteries. This series of pressures can consist of continuously variable or discrete period-wise constant values selected from 0 mmHg up to a pressure typically below the mean arterial pressure. One or more measurements may be performed at each value of externally-applied pressure. The waveforms of the pulse pressure are collected and models are fitted to these waveforms. By applying a lower external pressure (with respect to the blood pressure), blood pressure measurements can be effected in a non-invasive, non-occlusive way.

There are many methods of collecting the pulse pressure waveform data necessary for non-occlusive blood pressure measurement. In one embodiment, correlates of the blood volume displaced during each pulse are measured by recording pressure changes within the partially inflated fluid bladder placed around the arm, leg, wrist, or ankle. These are all sites amenable to the conventional Riva-Rocci method. However, since embodiments of the present invention are non-occlusive, measurement sites such as the fingers and toes are also suitable for application of the methods. This enables an embodiment in which the inflation device is miniaturized and incorporated into a finger ring, whereby signals from the digital arteries may be acquired using a conveniently wearable device.

Many methods have been proposed to calculate parameters of the cardiovascular system by analyzing pulse pressure waveforms. An embodiment of the current invention for estimating blood pressure is to calculate blood pressure (BP) from measurement pressure (MP), in which the logarithm of the amplitude (log A) of sensed pulses as a function of transmural pressure (TMP) on the artery is expressed as a straight line, specifically:

$$\log A = a\mathrm{TMP} + b + \mu \quad (1.1)$$

$$\text{because TMP} = \mathrm{BP} - \mathrm{MP} \quad (1.2), \text{we have}$$

$$\log A = a'\mathrm{MP} + b' + \mu' \quad (1.3)$$

a, b, a', and b' are coefficients, and $\mu$ and are errors of regression. Measurements of log A at at least two values of MP produce estimates of a' and b'. These are then used to estimate BP as: BP=f(MP, A, a', b', $\mu'$), in which f is a function of MP, A, a', b' and $\mu'$ or a subgroup of MP, A, a', b', and $\mu'$.

Alternatively, we can use the fitting of parameters in a multi-dimensional surface through multivariant regression, such as a plane surface, or multivariant linear regression, multivariant non-linear regression, principal component regression, machine learning, deep learning and neural networks. This also applies for the fitting of BP=f(MP, A, a', b', $\mu'$).

Since a' and b' can be obtained from fitting log A with MP, we teach a method that uses a subgroup of the variables to fit BP=f'(a',b'), and apply regression, machine learning, deep learning or neural networks to fit models. When applying a linear regression, we simplify the model into a plane surface in the 3D space. One benefit of this plane model is that, regardless of vascular tone, BP may be estimated for any (a',b') fitted to a series of log A as a function of MP, based on the MP value corresponding to the location of (a'b') on this plane. Another benefit of this plane model is that we can use as few as 3 sets of (BP, a', b') to identify this plane, which simplifies the calibration process.

Table 1 (FIG. 10) provides results of the fit of plane model in 5 subjects compared to standards of British Hypertension Society and US Association for the Advancement of Medical Instruments, and the $R^2$ of the fit of the plan models. CP is the cumulative percentage of difference between measured and calculated blood pressure smaller than a certain range. All of the 5 subject studies comply with both standards, and show great robustness regardless of the cardiovascular states and the position of the arm to the heart. The plane models are personalized models that represent the specific characteristics of the subject. By measuring the distention of the artery vs TMP, obtaining direct BP measurements, and fitting a plane model with as few as 3 data sets, we can accurately calculate blood pressure through analyzing pulse pressure waveforms. It is possible that a particular plane also represents the characteristic of a group of the general population who exhibit similar cardiovascular characteristics to a particular subject, or even, that by further understanding the link between this model with the cardiovascular characteristics of the subjects, we can develop generic models that apply to the large populations. Subject 1: female 33 years old, measurements taken over a time span of 2 weeks, under 3 conditions: rest, after upper body exercise (vasodilation) and after lower body exercise (vasoconstriction), and 4 relative positions to the heart: heart level, drop of arms, 10 cm, and 20 cm higher than the heart. The data were broken down into two parts. The first part was used to construct the model, and the second part, to calculate blood pressure using the constructed model, and to compare with the value measured by cuff sphygmomanometer (cross validation). Subject 2: male 40 years old, taken during 1 week and under 2 conditions: rest and after 20 mg of clonidine (maximum vasodilation), and 4 positions as above. The data were broken down into two parts, and used the same method as above. Subject 3: female 30 years old, taken over 2 weeks and under 2 conditions: rest and after abdominal and arm exercises, and 4 positions as above. The data were used to construct the model and the difference of the model and actual blood pressure was calculated. Subject 4: female 37 years old, taken over 2 weeks under 2 conditions: rest and after overall body exercise, and 4 positions as above. It was calculated in the same way as above. Subject 5: female 28 years old, one time rest condition. Calculated in the same way as above.

Another embodiment of analyzing pulse pressure is to fit the parameters of the waveforms, such as peak amplitudes, timing, and first and second derivatives with a pre-determined subject-specific or demographic-specific model. Another embodiment is to fit the above parameters with a generalized model based on large scale population study. Another embodiment is to fit the above parameters with models from self-calibration, in which previous data points will be analyzed to interpret newly collected data for blood pressure calculation.

In one embodiment of the present invention, accurate blood pressure is calculated from the models. In another embodiment, qualitative range, such as "Low"/"Acceptable Range"/"Elevated" or "Significantly Elevated", is reported, based on baselines (related to a specific individual or demographic) or pre-determined thresholds.

Building of Personalized Models

Another embodiment of this invention provides methods to build personalized models to facilitate accurate blood pressure calculation. The parameters of pulse pressure waveforms are calibrated against blood pressure measured from cuff sphygmomanometer or other non-invasive blood pressure measurements, or invasive blood pressure measurements if circumstances allow. Calibration can be performed on a beat-by-beat basis, which means that each of the pulse pressure peaks, feet, amplitudes, and other features are modeled against the corresponding blood pressure taken from the calibration device. Such calibration/model fitting can also be effected using the average characteristics of pulse pressure waveforms.

In one embodiment of a personalized model, a subject's blood pressure is characterized under conditions of different vascular tone, and/or relative height of the measurement point to the heart level. This involves using physical methods, such as upper, lower, or whole body prescribed motions/exercises to dilate or constrict the blood vessels, altering blood pressure in an artery by hydrostatic means by changing its vertical position relative to the heart, or medications that influence relevant parameters (blood pressure, vessel tone, venous pooling, cardiac output, nervous excitation) to realize controlled perturbation of the circulatory system. The set of convenient methods that can be used to characterize different operating points of the cardiovascular system include, for example:

Administering 400 micrograms of sublingual nitroglycerin. This will maximally dilate the majority of vessels in the arterial tree, lead to venous blood pooling, and increase systemic vascular resistance (SVR).

The Valsalva maneuver (where the subject blows against a pressure that opposes exhalation) inhibits venous return and leads to vasoconstriction and reduced cardiac stroke volume. This perturbation can be graded by requiring the subject to blow to match a set of prescribed pressures.

The Mueller maneuver (where the subject inhales against a pressure that opposes inhalation)

Tilting of the body can be used to determine the effects of different preload levels on the heart in order to characterize the relationship between the heart and the arterial system in an individual.

Inhalation of carbon dioxide (hypercapnia) increases BP, cardiac output and cardiac stroke volume. It also leads to vasodilation.

Another embodiment of building the personalized model is based on one or a few controlled perturbations without mapping the full circulatory system. This involves building the calibrated model based on collected data points and projecting the model to the full circulatory system.

Another embodiment of building the personalized model is to add additional measurements besides blood pressure into characterizing the circulatory system, in order to assist with calibration. These additional measurements include using ultrasound, ultra wideband (UWB), and tonometry to characterize vascular compliance and tone.

Another embodiment of building the personalized model is to apply demographic-specific or population-specific knowledge learned from previous measurements to project the parameters this individual under different vascular states.

Apparatus for Acquiring Pulse Pressure Waveforms

Another embodiment of this invention provides an apparatus for measuring pulse pressure waveforms for continuous/frequent non-invasive, non-occlusive blood pressure monitoring. The apparatus includes a pump, a band or cuff that provides slight inflation to add external pressure on the arteries, a pressure sensor to control the pressure applied by the band/cuff and collect pulse pressure waveforms. When taking measurements, the pump will inflate the band/cuff to apply external pressure on the arteries, and the sensor will track the pressure changes applied to the band/cuff as a result of the pulses of arteries.

One embodiment of the apparatus is shaped as a ring, with a biocompatible rubber-like material along the inside of the ring to apply the external pressure. Inflation is performed using a piezoelectric liquid pump, which is compact in size and exhibits low power consumption. The pressure sensor that tracks the pressure of the system will be connected to a microprocessor with wireless connectivity and internal memories to temporarily store data. A rechargeable battery is used to power the device.

In a variant of this embodiment, pressure is applied instead by a band which constitutes an adjustable tourniquet. The pressure exerted by this tourniquet can be calibrated to the strain or stress in the band, in general, or for a specific individual anatomy. A small bladder or other sensor (such as a load cell) may be located under the band to sense applied pressure. One embodiment of the invention is to add an accelerometer and/or gyroscope into the apparatus so that it can track the movement of the user and thus infer the activities of the user. This information can be used for doctors to understand how and why the blood pressure of the user varies over time. Optionally, the user (individual for whom the measurement is taken) may be alerted and asked questions by the device in order to determine the context of, or reason for a particular measurement, especially when a change in the measurement is not explicable in terms of otherwise monitored parameters.

Another embodiment of the invention is to add a wireless charging chip inside the apparatus, so that the ring can be charged remotely, or when put on top of a charging station. This will make it more convenient to use the ring.

Another embodiment of the invention is to add another layer of other biocompatible materials outside the rubber band or inflatable tube to provide increased comfort for the users.

Another embodiment of the invention is to configure the device as a wrist band. This provides another option for users who prefer a wrist band instead of a ring.

Another embodiment is to use a miniaturized air pump or piezoelectric air pump instead of a liquid pump for generating external pressure. Depending on the availability of component supplies and design, these alternatives can be incorporated into the apparatus.

Another embodiment is to add additional sensors, such as photoplethysmography (PPG), electrocardiogram (ECG), ultra-wideband (UWB), temperature, galvanic skin sensor (GSR), respiratory monitoring, and bioimpedance to assist with the characterization and analysis of pulse pressures. For example, the key insufficiency of using the PTT method to calculate blood pressure is the inability to account for the changing vascular tone (R A Payne, C N Symeonides, D J Webb, and S R J Maxwell. Pulse transit time measured from the ECG: an unreliable marker of beat-to-beat blood pressure. Journal of Applied Physiology, 100(1):136-141, 2006.), while the current invention teaches that by fitting the linear relationship of log A vs. MP, we can infer vascular tone and correct this confounding factor for the relationship between PTT and BP. Further, continuous monitoring of the pulse and respiration can help explain why blood pressure is varying, which is very important for effective ambulatory measurement. GSR can identify when nervous stress is the cause of acutely-elevated blood pressure.

Another embodiment is to select a pump with a wide range of pressure capability, which can apply enough pressure to occlude arteries. In this way, the device can serve as Riva-Rocci sphygmomanometer, and be used for measuring blood pressure to calibrate the device whenever/if needed.

Some further aspect of some embodiments of the current invention can include the following:
1. A method for blood pressure measurement whereby blood pressure is determined by examining the relationship between vessel distention and transmural pressure, via manipulation of the transmural pressure by application of a pressure to the arterial wall that is less than the diastolic pressure, or less than the systolic pressure.
2. The method of 1, where the pressure is applied by means of an inflatable cuff. The method of 1 where the pressure is applied using a band or tourniquet. The method of 1-3 where the pressure can be applied around one or more arteries.
3. The method of 1-2 where the pressure can consist of continuously variable or discrete period-wise constant values selected from 0 mmHg up to a pressure typically below the mean arterial pressure.
4. The method of 1-3 where one or more measurements may be performed at each value of externally-applied pressure.
5. The method of 1-4 where the vessel distension is measured as a pressure change in the cuff
6. The method of 1-5 where the vessel distension is measured as the change in strain on a band or tourniquet.
7. The method of 1-6 where pulse pressure waveforms are collected to measure vessel distension.
8. The method of 1-7 where the vessel distension is measured using ultrasound, or radar.
9. The method of 1-8 where the vessel distension is measured by recording pressure changes within the partially inflated fluid bladder placed around the arm, leg, wrist, or ankle.
10. The method of 1-8 where the vessel distension is measured by recording pressure changes within the partially inflated fluid bladder placed around sites such as the fingers and toes.
11. The method of 1-10 where the parameters of the collected pulse pressure waveforms, such as peak amplitudes, timing, and first and second derivatives are fitted with a pre-determined subject-specific or demographic-specific model.
12. The method of 1-10 where the parameters of the pulse pressure waveforms are fitted with a generalized model based on large scale population study.
13. The method of 1-10 where the parameters of the pulse pressure waveforms are fitted with models from self-calibration, in which previous data points will be analyzed to interpret newly collected data for blood pressure calculation.
14. The method of 1-13 where blood pressure is calculated from the models.
15. The method of 1-13 where qualitative range, such as "Low"/"Acceptable Range"/"Elevated" or "Significantly Elevated", is reported, based on baselines (related to a specific individual or demographic) or pre-determined thresholds.
16. The method of 1-15 where personalized models are built through calibration for accurate blood pressure measurements.
17. The method of 1-16 where calibration is performed against blood pressure measured from cuff sphygmomanometer or other non-invasive blood pressure measurements, or invasive blood pressure measurements if circumstances allow.
18. The method of 1-17 where calibration is performed on a beat-by-beat basis, which means that each of the pulse pressure peaks, feet, amplitudes, and other features are modeled against the corresponding blood pressure taken from the calibration device.
19. The method of 1-18 where calibration is performed using the average characteristics of pulse pressure pulse waveforms.
20. The method of 1-19 where a subject's blood pressure is characterized under conditions of different vascular tone, and/or relative height of the measurement point to the heart level.
21. The method of 1-20 where the perturbations for calibration are artificially induced.

22. The method of 1-21 where the perturbations include one or more of: administration of nitroglycerin, body tilting, altering the vertical height of a limb relative to the heart, Valsalva Maneuver, inhalation of carbon dioxide, administration of vasodilators, administration of vasoconstrictors, exercise, subjection to heat, subjection to cold, subjection to emotional stress.

23. The method of 1-22 where calibrations are based on mapping the full circulatory system of one subject or a group of subjects.

24. The method of 1-22 where calibrations are based on one or a few controlled perturbations without mapping the full circulatory system.

25. The method of 1-24 where calibrations are based on learning of demographic-specific or population-specific knowledge developed from previous measurements.

26. The method of 1-25 where calibration is assisted with additional measurements besides blood pressure into characterizing the circulatory system, such as using ultrasound, ultra-wideband (UWB), and tonometry to characterize vascular compliance and tone.

27. The method of 1-25 where blood pressure (BP) is calculated by utilizing the linear relationship of transmural pressure (TMP), or more the accessible measurement pressure (MP) with the logarithm of the amplitude of sensed pulses on the artery, such as $\log A = a\,TMP + b + \mu$ or $\log A = a'\,MP + b' + \mu$, and fitting with $BP = f(MP, A, a', b', \mu')$, or using a subgroup of those variables. The linear relationship is universal among different subjects, under different vascular tone, and at different positions relative to the heart.

28. The method of 1-27 where parameters are fitted in a multi-dimensional surface through multivariant regression, such as a plane surface, or multivariant linear regression, multivariant non-linear regression, principal component regression, machine learning, deep learning and neural networks.

29. The method of 1-28 where BP is fitted by $BP = f'(a', b')$ through regression, machine learning, deep learning or neural networks to fit models. Subject-specific and demographic-specific models can be built through these models.

30. The method of 1-29 where the models are simplified into a plane surface in the 3D space so that, regardless of vascular tone, BP may be estimated for any (a',b') fitted to a series of log A as a function of MP, based on the MP value corresponding to the location of (a', b') on this plane. This plane is consistently observed among different individuals, under different vascular tone, at different relative positions to the heart, and across longitudinal studies.

31. An apparatus for use with the method of 1-13 where the apparatus consists of a pump, a band or cuff that provides slight inflation to apply external pressure on the arteries, and a pressure sensor to control the pressure applied by the band/cuff and collect pulse pressure waveforms.

32. An apparatus for use with the method of 1-13 where the apparatus is shaped as a ring.

33. An apparatus for use with the method of 1-13 where the device is shaped as a wrist band.

34. An apparatus for use with the method of 1-13, and including the features of 32-33 where pressure is applied by a biocompatible material that is placed along the inside of the ring or wrist band.

35. An apparatus for use with the method of 1-13, and including the features of 32-33 where pressure is applied by a band which constitutes an adjustable tourniquet for a specific individual anatomy.

36. An apparatus for use with the method of 1-13, and including the features of 32-35 where another layer of other materials is added outside the inflatable band to provide increased comfort for the users.

37. An apparatus for use with the method of 1-13, and including the features of 32-36 where a piezoelectric pump is used for compact size and low power consumption.

38. An apparatus for use with the method of 1-13, and including the features of 32-37 where a rechargeable battery is used.

39. An apparatus for use with the method of 1-13, and including the features of 32-38 where an accelerometer and/or gyroscope is put into the apparatus to track movement and thus infer the activities of the user.

40. An apparatus for use with the method of 1-13, and including the features of 32-39 where a wireless charging chip is added for convenience in charging.

41. An apparatus for use with the method of 1-13, and including the features of 32-40 where the device use miniaturized air pump or piezoelectric air pump instead of liquid pump for generating external pressure.

42. An apparatus for use with the method of 1-13, and including the features of 32-41 where additional sensors, such as photoplethysmography (PPG), electrocardiogram (ECG), ultra wideband (UWB), temperature, galvanic skin sensor (GSR), respiratory monitoring, and bioimpedance are added to assist with the characterization and analysis of pulse pressures.

43. The method of 1-13, and including the features of 32-42, where the apparatus determines when to initiate a measurement of blood pressure, based on sensed activity and/or changes in other physiological variables.

44. A method of 43 in which the user is prompted to explain possible reasons for an observed change in blood pressure and/or other physiological variables.

45. A method of 45 in which multiple choice options are provided to enable the user to quickly select among the most probable causes of the observed pressure change.

46. A method of 43-45 in which a voice prompt asks the questions.

47. A method of 43-46 in which the user may answer using vocal communication.

2. Personalized Non-Invasive, Non-Occlusive Blood Pressure Measurement Using Oscillometric Waveform Analysis The following embodiments of present invention relate to the methods and apparatuses for blood pressure monitoring by characterizing the oscillometric waveforms on an individual basis to achieve non-invasive, non-occlusive blood pressure measurement. In particular, it relates to methods and apparatuses of simulating the oscillometric waveforms of an individual through characterizing the full or partial oscillometric waveforms collected from this individual or population with similar physiological characteristics, and use the parameters from this simulation to calculate new blood pressure values based on partial oscillometric waveforms newly collected for this individual to realize non-invasive, non-occlusive blood pressure measurement. The replacement of the need of always collecting the full oscillometric waveforms to calculate blood pressure with the methods of collecting partial oscillometric waveforms, for example, up to pressures less than the mean arterial pressure, enables the design of an apparatus that measures blood pressure with less unloading pressure on the artery, uses less power, and has a miniaturized form factor to realize comfortable, high frequency, wearable blood pressure monitoring. In some embodiments, the characterization of the oscillometric waveforms can be obtained through a standalone oscillometric device, and in some other embodiments, the characterization of the oscillometric waveforms can be obtained through the same device that offers non-invasive, non-occlusive blood pressure monitoring.

We use the term "high frequency" to refer to an ability to obtain frequent estimates of full or partial oscillometric waveforms, or both. Depending on the needs, "high frequency" varies from 24 hour blood pressure data over days, months, or years, or repeated measurements within a short period of time, such as less than an hour, several hours, or days.

Some embodiments of the present invention provide methods for non-invasive, non-occlusive blood pressure monitoring by analyzing the partial oscillometric waveforms of an individual to calculate blood pressure. Another embodiment of the present invention provides an apparatus for providing high frequent, non-invasive, non-occlusive blood pressure monitoring by collecting oscillometric waveforms.

An embodiment of the current invention provides methods to fit the partial oscillometric waveforms with mathematical models to calculate blood pressure. This is executed by first simulating the oscillometric waveforms of an individual under different vascular tone through characterizing the full or partial oscillometric waveforms collected from this individual or population with physiological characters similar to this individual, and then use the parameters from this simulation to calculate blood pressure in a non-invasive, non-occlusive way. The theory behind the mathematical models is a pressure-volume model that characterizes the relationship of transmural pressure ($P_t$, which is the difference between the lumen of the artery and the exterior of the wall of the same artery, and calculated as $P_t=BP-P$, where BP is the blood pressure and P is measuring unloading pressure) with arterial volume (V). This pressure-volume relationship can be approximated by various models, such as exponential equations (Charles F Babbs. Oscillometric measurement of systolic and diastolic blood pressures validated in a physiologic mathematical model. Biomedical engineering online, 11(1):1, 2012; P D Baker, Dwayne R Westenskow, and K Kück. Theoretical analysis of non-invasive oscillometric maximum amplitude algorithm for estimating mean blood pressure. Medical and biological engineering and computing, 35(3):271-278, 1997.), tangential equations (Mohamad Forouzanfar, Balakumar Balasingam, Hilmi R Dajani, Voicu Z Groza, Miodrag Bolic, Sreeraman Rajan, and Emil M Petriu. Mathematical modeling and parameter estimation of blood pressure oscillometric waveform. In Medical Measurements and Applications Proceedings (MeMeA), 2012 IEEE International Symposium on, pages 1-6. IEEE, 2012; Jiankun Liu, Hao-Min Cheng, Chen-Huan Chen, Shih-Hsien Sung, Mohsen Moslehpour, Jin-Oh Hahn, and Ramakrishna Mukkamala. Patient-specific oscillometric blood pressure measurement. IEEE Transactions on Biomedical Engineering, 63(6):1220-1228, 2016.), or any least square equations fitted by empirical data. Those models contain physiological parameters that can be fitted with data points that profile the change of pulse pressure with regards to a changing unloading pressure from above the systolic pressure all the way to below the diastolic pressure. The current invention teaches that by using a partial oscillometric waveform, blood pressure can be obtained by understanding the parameters for the oscillometric waveforms.

In an embodiment of the invention, an exponential model is used to simulate the pressure-volume relationship, which derives a linear relationship of the logarithm of the pulse amplitude ($\ln(\Delta P)$) with P for both the rising and falling phases of an oscillometric waveform (P>SBP or P<DBP). Thanks to these linear relationships, the entire waveform can be extrapolated by only collecting part of the waveform through a few number of data points. In some embodiments, to reinforce the mathematical models, a combination of full and partial oscillometric waveforms, or a combination of partial oscillometric waveforms of different lengths or P ranges can be used to assist with getting accurate blood pressure calculation.

Another embodiment of this invention provides an apparatus to collect partial or a combination of partial and full oscillometric waveforms to calculate blood pressure. An embodiment can be a wrist worn device that includes a pressure adjustment mechanism, a pressure sensor, and a pressurized bladder to load and sense pressure around the wrist. In some embodiments, blood pressure readings will only be reported through the analysis of full oscillometric waveforms or a few partial oscillometric waveforms, and the analysis of partial oscillometric waveforms will mainly serve as passive monitoring for records or to alert potential abnormal blood pressure conditions. In other embodiments, the apparatus includes battery and AC power options to meet the different power needs of generating partial or full oscillometric waveforms. In some other embodiments, the apparatus provides heart rate readings, or includes other physiological sensors such as photoplethysmogram (PPG) or electrocardiogram (ECG) to assist with the monitoring of blood pressure and other physiological parameters. In some other embodiments, other physiological sensors are used to provide more frequent blood pressure measurements in between the use of pressure actuation. In some other embodiments, the apparatus includes the use of an accelerometer and gyroscope to infer the activity of the user, so that blood pressure measurements can be better interpreted with respect to context. In some other embodiments, the apparatus serves as a hardware platform to infer other physiological parameters, such as arterial stiffness, blood oxygenation, breathing rate, cardiac output, central venous pressure, etc., build a 24 hour profile of cardiovascular parameters that can be baselined, compared, and interpreted, and evolve into a data collection, interacting and analyzing platform for cardiovascular wellness.

FIGS. 11A-C show an illustration of top, bottom, and side views, respectively, of an embodiment of the apparatus for frequent non-occlusive blood pressure measurement based on partial oscillometric waveform analysis. It is designed as a wrist band, using miniaturized components. 1 is a band that wraps around the wrist to hold 2 the enclosure for the electronics, which has an optional low-power LED display. 3 is a micro pump, and 4 is a PCB board with sensors, battery, and optional wireless module. 5 is marks for the users to track the fit of the band, and 6 is a buckle to secure the band with 5. 7 is a bladder that is attached under the wrist band to apply and sense pressures around the artery. 8 is a port for charging and data output/input, while 9 is a control button. Both 8 and 9 are optional, and can be rearranged or redesigned. The sizes of each component can be adjusted, and the buckle mechanism can be changed to other mechanisms to secure the band around the wrist and maintain consistent measurement conditions.

Figure 12A:
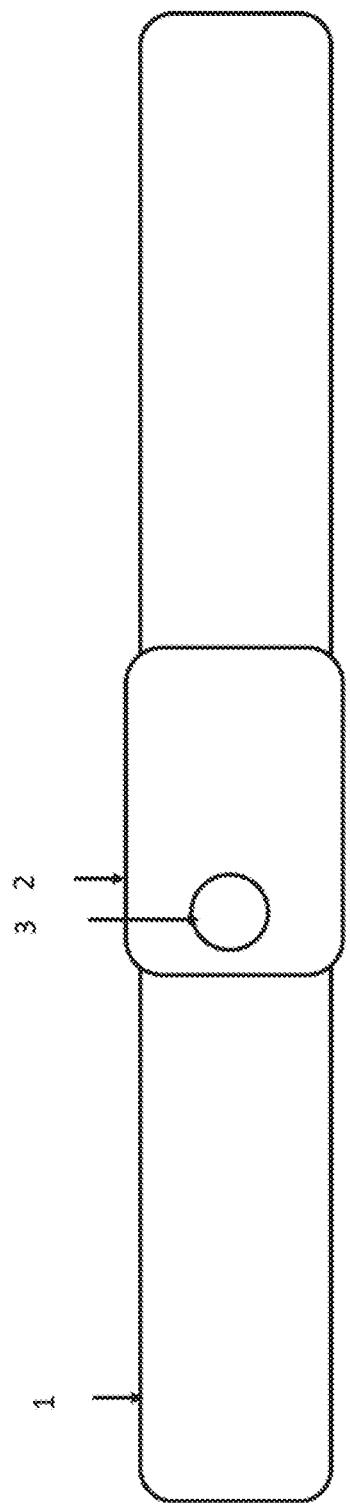
FIGS. 12A and 12B show top and bottom views, respectively, of a blood pressure monitoring device according to another embodiment of the current invention.
Figure 12B:
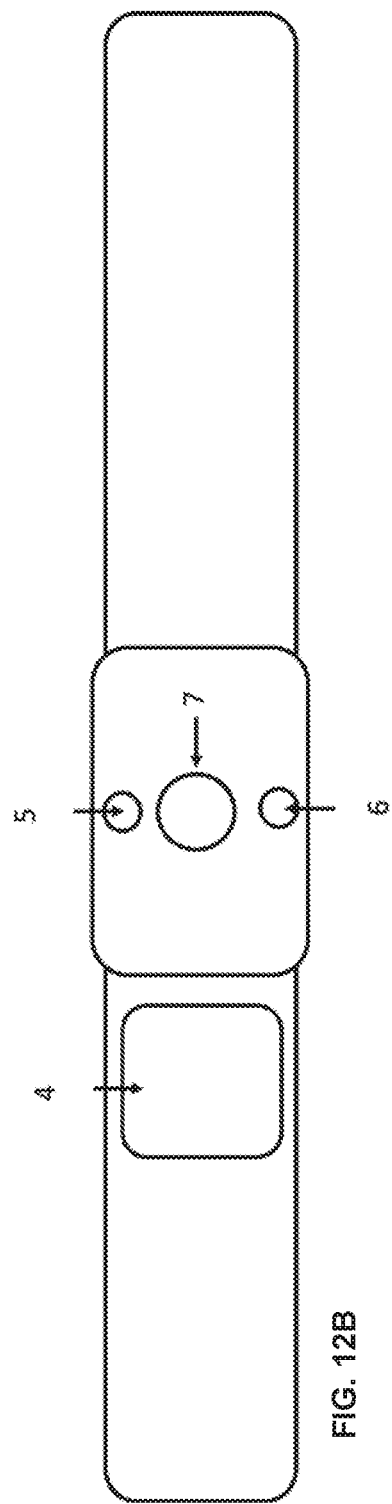

FIGS. 12A and 12B are top and bottom views, respectively, of another embodiment of an apparatus for frequent non-occlusive blood pressure measurement based on partial oscillometric waveform analysis. 1 is a wrist band that can be fastened along the wrist, 2 is the electronic compartment that contains PCB, a microcontroller, a battery, a pump, wireless module, memory, and an optional low-power LED display. 3 and 7 are the two electrodes of ECG that will form a circuit when the device is worn on the wrist and a finger of the user from the other arm touches 3. 5 and 6 are PPG sensors. 4 is a small-sized bladder that captures pulse pressure waveforms.

DETAILED DESCRIPTION

This embodiment of the current invention uses one or multiple partial oscillometric waveforms to fit with the unique relationships of the parameters of a full oscillometric waveform in order to calculate blood pressure for an individual without always applying external pressures above the systolic pressure. Some advantages of this embodiment can include less power consumption, improved comfort to the user, and the possibility of miniaturizing hardware components to a wearable device. A full oscillometric waveform is defined as first increasing the unloading pressure to the artery to above the systolic pressure, and then use a bleed mechanism to reduce the pressure at a constant pace all the way to below the diastolic pressure, or a lower pressure close to 0 mmHg. A partial oscillometric waveform is defined as one segment of the full waveform, such as in a pressure range from lower than the diastolic pressure to above 0 mmHg. The theories supporting this embodiment of the invention are characterization of the compliance of arteries through a volume-pressure model, and by fitting the full or partial oscillometric waveforms of an individual or a group of individuals with similar vascular parameters, we can build models for calculating both systolic and diastolic blood pressures under different vascular tone, individual characteristics, and measurement conditions. With an initial characterization of full or partial oscillometric waveforms, the partial oscillometric waveforms of an individual can provide enough information to derive the parameters to simulate the full oscillometric waveform for an individual, and thus calculate both systolic and diastolic pressures through a device that applies light pressures on the artery and collect signals of the oscillations of pulses.

Calculating Blood Pressure from Partial Waveforms

An embodiment of the current invention provides methods to calculate BP by analyzing partial oscillometric waveforms. According to the exponential pressure-volume model of the arteries, the volume of the arteries (V) with regards to transmural pressure ($P_t$) follows:

$$V = \begin{cases} V_0 e^{aP_t} & P_t \leq 0 \\ V_{max} + (V_0 - V_{max})e^{bP_t} & P_t \geq 0 \end{cases} \quad (2.1)$$

where V is the volume of the artery for a specific transmural pressure $P_t$, $V_0$ is the volume of the artery when the transmural pressure is zero (when external pressure equals to mean arterial pressure), $V_{max}$ is the volume of the artery when it is fully expanded, and a and b are exponential coefficients that depend on the compliance of the blood vessels. Specifically, we have:

$$a = \frac{C_{max}}{V_0} \quad (2.2)$$

$$b = -\frac{C_{max}}{V_{max} - V_0} \quad (2.3)$$

where $C_{max}$ is the maximum compliance in the P-V relationship, which depends on the vascular state of a person and occurs at zero transmural pressure. As compliance is defined as the change of artery volume with regard to change of transmural pressure $$\left(\frac{\Delta V}{\Delta P_t}\right),$$

the pulsatile change in the cuff pressure ΔP can be simulated by the following equations:

$$\Delta P = \begin{cases} \frac{V_0}{C_{cuff}}(e^{a \times SBP} - e^{a \times DBP}) \times e^{-a \times P} & P > SBP \\ \frac{V_0}{C_{cuff}}\left(1 - \frac{a}{b}(1 - e^{b \times (SBP-P)}) - e^{a \times (DBP-P)}\right) & SBP \geq P \geq DBP \\ \frac{V_0}{C_{cuff}} \times \frac{a}{b} \times (e^{b \times DBP} - e^{b \times SBP}) \times e^{-b \times P} & P < DBP \end{cases} \quad (2.4)$$

P is the unloading pressure of the cuff, SBP is the systolic pressure, DBP is the diastolic pressure, and $C_{cuff}$ is effective compliance of the cuff, which can be approximated as a constant if the measuring condition of the cuff stays the same. Further, the first and third equation in (2.4) can be simplified as a linear relationship:

$$Ln(\Delta P) = \begin{cases} \ln\left(\frac{V_0}{C_{cuff}}(e^{a \times SBP} - e^{a \times DBP})\right) - a \times P & P > SBP \\ \ln\left(\frac{V_0}{C_{cuff}} \times \frac{a}{b} \times (e^{b \times DBP} - e^{b \times SBP})\right) - b \times P & P < DBP \end{cases} \quad (2.5)$$

This linear relationship has been supported by our previous empirical findings (U.S. Provisional Patent No. 62/290, 642), which simplifies parameter fitting and calculation.

From a full oscillometric waveform, we can obtain personalized parameters such as $V_0$, $C_{cuff}$, $C_{max}$, and $V_{max}$ from equations (2.2), (2.3), and (2.4). This will be done by first calculating DBP and SBP through traditional methods, such as Korotkoff sounds or validated automatic blood pressure monitors. For the same individual, if there is no drastic physiological change, $V_0$ is a constant that can be calibrated on an individual basis, and $C_{cuff}$ is a constant if measurements are controlled to be under the same cuff tightness and speed of inflation. Therefore, calibration using the full oscillometric waveform can accurately calibrate individual-specific parameters such as $V_0$ and $C_{cuff}$. $V_{max}$ varies with smooth muscle regulation, and together with maximum compliance $C_{max}$, changes with various internal and external factors for an individual, such as medication, physical activity, temperature, mood, and health conditions. Therefore, from a full oscillometric waveform and given equations of (2.2) and (2.3), we can obtain the amplitude of the pulse wave forms Ln(ΔP) as a function of SBP, DBP, $C_{max}$, $V_{max}$ and P. By simulating the changes of Ln(ΔP) with SBP, DBP, $C_{max}$, $V_{max}$ and P for the segment of P<DBP, and by incorporating the linear relationship of P and Ln($\Delta$P) of equation (2.5), we can generate a function of Ln($\Delta$P)=F (DBP, SBP, i), in which i is an indicator of the arterial state, which represents the arterial compliance and smooth muscle regulation. The current invention teaches that i is a function of parameter b, or i=g(b), and also that through simulation results based on human cardiovascular parameters, the impact of SBP to Ln($\Delta$P) is very small in function F. Since b is an parameter that can be easily obtained through the linear relationship in equation (2.5), we have Ln($\Delta$P)=f (DBP, b, u) to represent the relationship of Ln($\Delta$P) with DBP for a given state in the P<DBP segment of the oscillometric waveform, and u is an error term. This theoretical analysis support the claims of the U.S. Provisional Patent No. 62/290,642.

An embodiment of obtaining personalized parameters such as $V_0$ and $C_{cuff}$, is to use a partial oscillometric waveform instead of a full waveform, preferably by inflating to a pressure less than systolic pressure and above the mean arterial pressure, and bleeding to less than diastolic pressure. The SBP can be obtained by measuring the pulse amplitude with regard to the peak height of the waveform, and by plugging into the domain 2 and 3 of equation (2.4), or SBP≥P≥DBP and P<DBP, parameters such as $V_0$ and $C_{cuff}$ can be obtained.

Once the initial parameters are obtained, to take blood pressure measurements, a new measurement of a partial oscillometric waveform is collected by inflating to a pressure less than DBP and bleeding down to a lower pressure. This waveform falls into the third domain of equation (2.5) for P<DBP. At this second measurement, the state changes to i' which is represented by b', the slope of the new linear fit. With Ln($\Delta$P)=f(DBP, b', u), we can obtain DBP.

In another embodiment of this invention, personalized parameters can be obtained by generating multiple full or partial oscillometric waveforms. These waveforms are preferably obtained representative of different vascular tone, induced by perturbations such as physical activities or medications. This could build a sophisticated model on i=g(b) in addition to $V_0$ and $C_{cuff}$ to increase the accuracy of parameter fitting. Once the initial parameters are obtained, with the partial oscillometric waveform, we can use Ln($\Delta$P)=f(DBP, u) to obtain DBP for a new state i'.

An embodiment of calculating SBP is based on the fact that the pulse amplitude $\Delta$P is proportional to the pulse pressure PP (PP=SBP−DBP), or $$PP = r \times \Delta P \qquad (2.6)$$

and the ratio r is a function of measurement pressure P and arterial compliance, represented by state i. This invention teaches that for a given DBP, the change of arterial compliance with measurement pressure is uniquely related to the ratio of r, or r=h(P, i). With a full oscillometric waveform, we can take the advantage of the linear relationship of Ln($\Delta$P) with P, and also simulate lines of how Ln(r) changes with P for different i. When we take the second measurement for a partial oscillometric waveform, after we calculate DBP for this partial waveform, we can identify which r=h(P, $_i$) line it falls in, and thus derive PP to calculate SBP.

Another embodiment of calculating SBP is using a partial oscillometric waveform obtained by inflating to a pressure less than systolic pressure and greater than diastolic pressure, and bleeding down to less than diastolic pressure. This partial waveform covers two domains of equation (2.4): SBP≥P≥DBP and P<DBP. In the first domain, SBP has significant impact on the shape of the curve, or Ln($\Delta$P)=f' (DBP, SBP, i). After we obtained DBP from the second domain through Ln($\Delta$P)=f(DBP, i), we can solve for SBP through f'.

Another embodiment of calculating SBP and DBP is using other models, such as pressure-flow propagation model (Ryu J, Hu X, Shadden S C. A Coupled Lumped-Parameter and Distributed Network Model for Cerebral Pulse-Wave Hemodynamics. J Biomech Eng. 137(10): 101009, 2015.) or pulse transit time (PTT) model, to augment the parameter fitting of the pressure-volume model. For example, the PTT model can be related to pulse wave velocity (Bramwell J C and Hill A V, The velocity of the pulse wave in man, Proceedings of the Royal Society of London. Series B. 93 (652): 298-306, 1922), which is a function of blood vessel volume and compliance, and help identify parameters such as $V_0$ and i.

Figure 13:
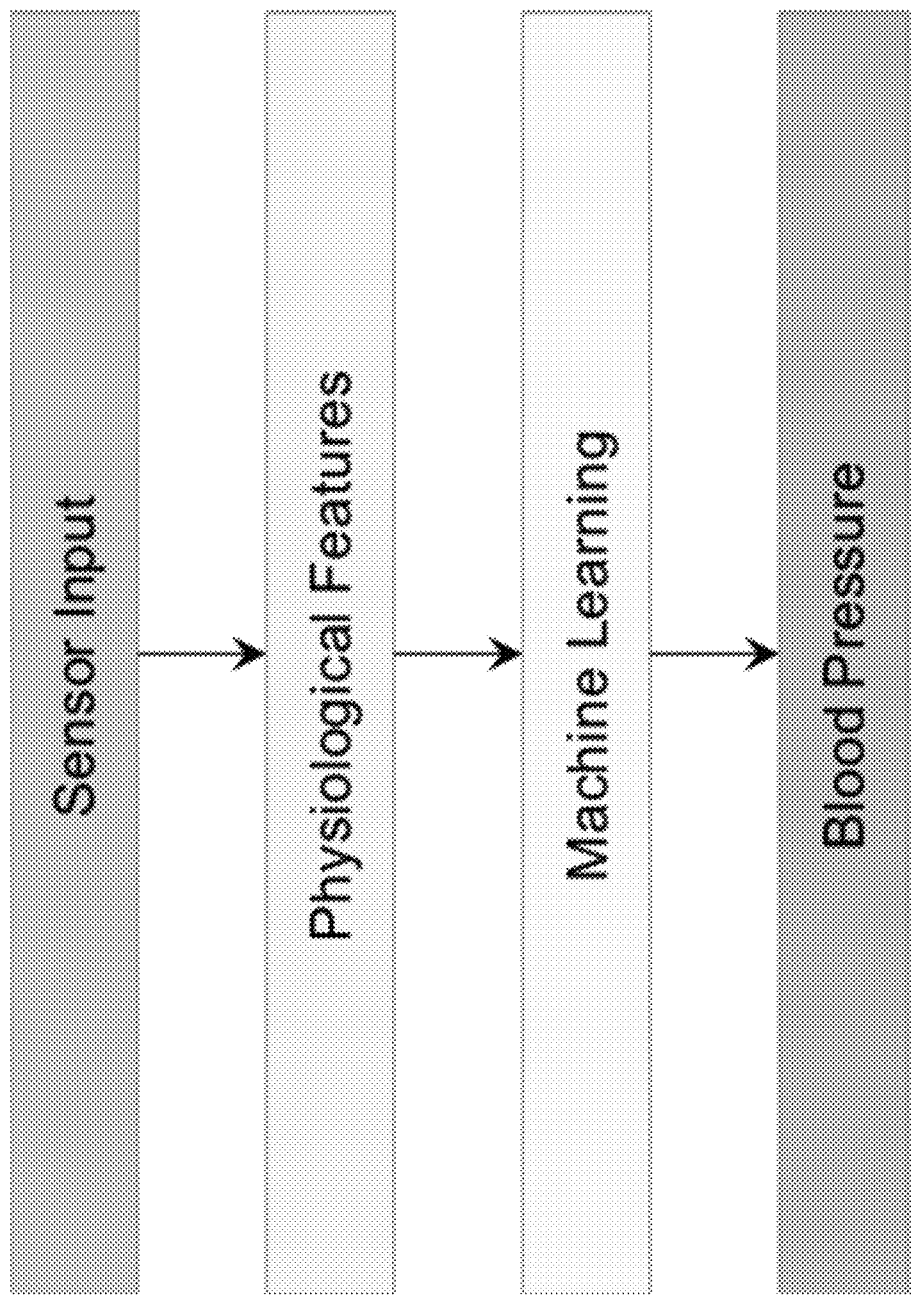
FIG. 13 is a schematic illustration of using machine learning on top of physiological features extracted from sensor input such as a, b, a', b' to build sophisticated models to calculate blood pressure.

Another embodiment of calculating SBP and DBP is using machine learning to improve the accuracy of calculation. FIG. 13 illustrate the process of extracting physiological features from sensor data, and use machine learning to calculate blood pressure. The physiological features can include demographic information, physiological parameters obtained through calibration, relationship of certain parameters established by theoretical and empirical models, and etc.

Figure 14:
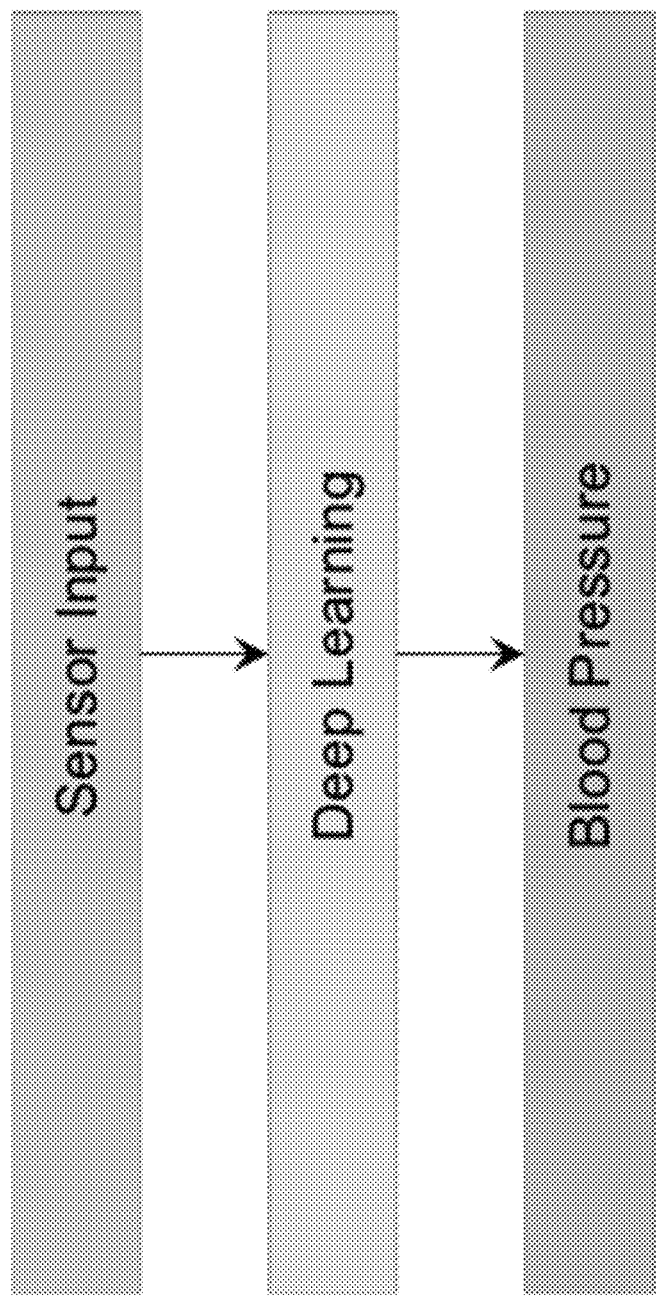
FIG. 14 is a schematic illustration of applying deep learning on sensor input to calculate blood pressure.

Another embodiment of calculating SBP and DBP is using deep learning directly from sensor input. FIG. 14 illustrate the process. In some embodiments, certain important parameters or will be characterized through deep learning.

In some other embodiments, through machine and deep learning, we can eliminate need for calibration, either the initial parameter fitting or throughout the life time of the device. The use scenario can be that a patient will get the device from the doctor through mail, put the device on, and the device will start taking measurements with very simple or minimal setup required from the patient.

Apparatus for Partial Oscillometric Waveform for Calculating Blood Pressure

Another embodiment of this invention provides an apparatus for collecting partial oscillometric waveforms for calculating blood pressure. The preferred embodiment is a wrist-worn band that includes a pressure adjustment mechanism (for example, a micro pump, a piezoelectric pump, a servo motor or a shape memory alloy actuator), a pressure sensor, a microcontroller, a rechargeable battery, a blue tooth or WiFi module for wireless connectivity, and a bladder that can be applied around the wrist for applying pressure and sensing the oscillometric waveforms. The components are miniaturized according to a maximum unloading pressure less than the diastolic pressure, such as 80 mmHg, so that it always collects partial waveforms. Benefits of applying low pressures include reducing power consumption and component sizes so that the device has optimal wearability. There are markers on the band of the wrist-worn device for users to wear the device at the same tightness. The proper initial pressure can also be set more accurately using the internal pressure sensor and a LED indicator. This embodiment may be calibrated by a stationary blood pressure monitor that collects full oscillometric waveforms and provides systolic and diastolic pressures readings. One or multiple waveforms may be obtained for this calibration that generates personalized parameters. The device may only need to be recalibrated once every year or longer, or after drastic physiological changes. This design of calibration is suitable for a hospital setting, where the nurses have one calibration device to calibrate the individual devices from the users. The systolic and diastolic pressures can also be obtained by the Korotkoff sounds method through the stationary device or manually by a technician.

One embodiment of this invention is to obtain personalized parameters through an add-on device that increases the maximum pressure that can be applied to the artery, so that a full or longer partial oscillometric waveform can be obtained. This add-on device includes an additional pump and power supply, and will be connected through a port on the wrist-worn device that has two connectors, one for the power, and the other for connection into the inflation system. The power supply of the add-on device can be batteries, through wireless charging or through AC adapters. This add-on device can increase the frequency of calibration, and can be done outside of clinics.

In another embodiment, the maximum pressure of the wrist-worn device can be increased so that a longer partial waveform or a full waveform can be obtained. Additional power supply through batteries or AC power may be implemented to support the power needs of collecting full or partial waveforms with a starting pressure above the diastolic pressure. With this design, the device can be calibrated on its own.

In another embodiment, blood pressure readings can be obtained through both full occlusion (analyzing the full oscillometric waveforms) and non-occlusion (analyzing the partial waveforms). In a variant of this embodiment, blood pressure readings can be only obtained through the full occlusion mechanism, while the partial occlusion only serves as passive monitoring of blood pressure variation, and support an alert system for reminding the user to use the full occlusion method to get blood pressure readings. This embodiment is suitable for situations when the doctors recommend the users to measure blood pressure consistently and only a few times per day, while the device can still catch sudden surge of blood pressure. In a variant of this embodiment, the pressure used to generate partial oscillometric waveforms may be set very low to reduce power consumption and increase comfort.

In another embodiment, this non-occlusive blood pressure monitoring can be performed through a cuff-based blood pressure monitor, with improved comfort. This can be done by incorporating the algorithm into the hardware of an automatic blood pressure monitor.

In another embodiment, the apparatus can be made into a device around any arteries, such as around the arm, leg, neck, ankle, or fingers.

In another embodiment, automatic sensing mechanisms will guide the fastening of the band, so that pressure actuation always starts from the same initial condition, such as tightness, pressure, and apparatus location on the wrist.

In another embodiment, motion sensors such as accelerometer and gyroscope can be implemented to assist with the calibration of blood pressure at heart level, so that users don't have to always measure blood pressure at the heart level in order to have data that can be compared at the same basis. The use of motion sensors can also infer the activities of the users in order to assist with the interpretation of blood pressure data.

In another embodiment, heart rate readings can be provided by the apparatus by counting the number of pulses within a given time.

In another embodiment, additional sensors, such as photoplethysmography (PPG), electrocardiogram (ECG), ultra wideband (UWB), temperature, galvanic skin sensor (GSR), respiratory monitoring, and bioimpedance can be used to assist with the characterization and analysis of partial oscillometric waveforms. Those additional sensors can help build additional models such as pressure-flow propagation models or PTT models. In some other embodiments, those sensor data can be used for machine learning and deep learning for improved accuracy. In some other embodiments, those additional sensors will provide more frequent blood pressure monitoring in between the use of pressure actuation. Because the key insufficiency of using PTT method for blood pressure is the confounding factors of vascular tone, and currently the way to correct those effects is frequent calibration against a cuff monitor or other validated methods, by using the partial oscillometric waveform, the apparatus can automatically calibrate the PTT method by itself, so that higher frequent blood pressure monitoring up to beat-to-beat monitoring can be achieved.

In some other embodiments, the apparatus has both wireless connectivity and cloud access, through which data from the apparatus can be transferred to proper storage and analyzing platform for further processing. Those platforms include mobile applications, cloud storage and computation, electronic health record, or other APIs.

In some other embodiments, the apparatus has a user interface that consist of one or both of a mobile application and a low-power LED screen that enables interactions between the user and the device. The mobile application can have a dashboard of blood pressure and other cardiovascular parameters, history and trendline, and areas for the user to log in other related information. In some other embodiments, the apparatus also consists of an interface with the doctors, either directly through the cloud or through an electronic health record system. The interface with the doctor can include statistics of blood pressure and other cardiovascular parameters, such as average, standard deviation, percentage of time when blood pressure is at certain level, the option for zoning in to a certain time period and perform analysis, the correlation of blood pressure with patient's behaviors and activities, and other information to help doctors understand the patient's health.

In some other embodiments, the apparatus serves as a hardware platform to infer other physiological parameters, such as arterial stiffness, blood oxygenation, breathing rate, cardiac output, central venous pressure, etc. The assessment of arterial stiffness can be inferred from vascular tone obtained from parameters such as $V_{max}$, $C_{max}$, b and a, or calculated from models built from those features. Blood oxygenation can be obtained by using two PPG sensors with different wavelength. Other parameters, such as breathing rate, cardiac output, central venous pressure can be calculated from both schemes in FIG. 13 and FIG. 14.

In some other embodiments, the user interface provides alerts for blood pressures that are "Low', "Medium" or "High", and provide interpretation the reason for blood pressure changes. This can be done by building a 24 hour profile of an individual's blood pressure and other cardiovascular parameters, correlations of those parameters with activity, diet, medication, environmental factors, and mood, etc., understanding baseline variations of blood pressure and other cardiovascular parameters, identify abnormal conditions, and provide interpretation. This can be done through machine learning and deep learning of individual data as well as demographic-specific or population-specific data.

In some other embodiments, the user interface provides alerts or reminders for medication, physical exercise, sleep, and other interventions to help user become compliant with intervention and to increase the efficacy of monitoring blood pressure and other cardiovascular parameters. In this way, a positive feedback loop can be established to improve clinical outcome of monitoring patients with cardiovascular diseases. In some other embodiments, the user interface provides communication with family members, doctors, nurses, care takers, and people in a community from the user or from the device.

In some other embodiments, adaptive monitoring will be implemented based on sensor data. For example, accelerator and gyroscope can provide motion information to help the apparatus to decide when to take measurements in addition to filter out bad signals. The learning from building 24 hour personalized models, medical records, and other information about the user can also infer the best time to take measurements to obtain the most representative data about the user's health conditions.

In some other embodiments, an expert system on human cardiovascular health can be built through machine learning, deep learning, and other artificial intelligence algorithms to provide a second opinion to doctors on diagnosis and treatment.

In some other embodiments, the apparatus can be built into the form of a watch. In some other embodiments, the apparatus provides time and time-stamped data.

Some embodiments of the current invention can include the following features:

1. A method for determining blood pressure measurement, comprising analyzing partial oscillometric waveforms of an artery, to realize non-occlusive, non-invasive blood pressure monitoring. This entails the characterizing of personalized parameters through one or multiple full or partial oscillometric waveforms of an individual through simulation based on a pressure-volume model for the arteries, and then fitting partial oscillometric waveforms to simulated models to derive both systolic and diastolic pressures.
2. The method of 1, wherein replacement of the need of always collecting the full oscillometric waveforms to calculate blood pressure enables the design of an apparatus with miniaturized pressure adjustment mechanism, such as micro pumps or a shape memory alloy actuator, that measures blood pressure with less unloading pressure on the artery, uses less power, and in a miniaturized form factor to realize comfortable, high frequency, wearable blood pressure monitoring.
3. The method of any one of 1-2, wherein full or partial oscillometric waveforms are used for characterizing the personalized physiological parameters of an individual.
4. The method of any one of 1-3, wherein the characterization of the personalized physiological parameters can be obtained through a standalone oscillometric device.
5. The method of any one of 1-3, wherein the characterization of the personalized physiological parameters can be obtained through the same device that offers non-invasive, non-occlusive blood pressure monitoring through analyzing partial oscillometric waveforms.
6. The method of any one of 1-5, wherein simulations of oscillometric waveforms of an individual are implemented based on parameters obtained from characterizing the full or partial oscillometric waveforms of this individual to calculate blood pressure with partial oscillometric waveforms.
7. The method of any one of 1-5, wherein simulations of oscillometric waveforms of population with similar physiological characters are implemented to calculate blood pressure of an individual with similar physiological characters through his or her partial oscillometric waveforms.
8. The method of any one of 1-5, wherein pressure-volume models that characterize the relationship of transmural pressure with arterial volume (V) is used to build the simulation of oscillometric waveforms.
9. The method of any one of 1-8, wherein the partial oscillometric waveforms of an individual provide enough information to project the full oscillometric waveform for this individual, and thus to calculate both systolic and diastolic blood pressures.
10. The method of any one of 1-9, wherein a full oscillometric waveform is used to obtain personalized parameters such as $V_0$, $C_{cuff}$, $C_{max}$ and $V_{max}$.
11. The method of any one of 1-9, wherein a partial oscillometric waveform instead of a full waveform, preferably by inflating to a pressure less than systolic pressure and above the mean arterial pressure, and bleeding to less than diastolic pressure is used to obtain personalized parameters such as $V_0$, $C_{cuff}$, $C_{max}$ and $V_{max}$.
12. The method of any one of 1-11, wherein personalized parameters can be obtained by collecting multiple full or partial oscillometric waveforms.
13. The methods of any one of 1-12, wherein multiple full or partial oscillometric waveforms representative of different vascular tone, induced by perturbations such as physical activities or medications are obtained to increase the accuracy of parameter fitting.
14. The methods of any one of 1-13, wherein the amplitude of the pulse wave forms $Ln(\Delta P)$ can be modeled as a function of SBP, DBP, $C_{max}$, $V_{max}$ and P, and by simulating the changes of $Ln(\Delta P)$ with SBP, DBP, we can derive $Ln(\Delta P)=f(DBP, i)$ for P<DBP that well represents the relationship of measured amplitude with DBP for given vascular state represented by i.
15. The methods of any one of 1-14, wherein a partial oscillometric waveform in the range of P<DBP is obtained to fit the model $Ln(\Delta P)=f(DBP, b')$ with a new b' to obtain DBP.
16. The methods of any one of 1-13, wherein the ratio of pulse amplitude $\Delta P$ to pulse pressure PP can be modeled and simulated with $r=h(P, i)$, or the linear relationship of its logarithmic form.
17. The methods of any one of 1-13 and 16, wherein one or multiple full or partial oscillometric waveform is used to calibrate the simulation of $r=h(P, i)$, and the change of vascular tone (represented by i) with measurement pressure P is uniquely related to ratio r for a given DBP.
18. The methods of any one of 1-17, wherein one or multiple partial oscillometric waveform in the range of P<DBP is obtained to fit into the calibrated simulation of rh(P, i) to derive PP, and thus calculate SBP.
19. The methods of any one of 1-15, wherein SBP is calculated by using a partial oscillometric waveform covering the ranges of SBP≥P≥DBP and P<DBP that fits into the model of $Ln(\Delta P)=f'(DBP, SBP, i)$.
20. An apparatus for measuring blood pressure in a non-invasive, non-occlusive way, preferably a wearable device such as a wrist-worn band, that consists of a pressure adjustment mechanism (micro air or liquid pump or servo motor or a shape memory alloy actuator), a pressure sensor, a microcontroller, a rechargeable battery, a blue tooth or WiFi module, and a bladder that can be applied around the wrist for applying pressure and sensing the oscillometric waveforms.

21. The apparatus of 20, wherein there are markers on the band with the bladder for the users to fit the band with the same tightness each time to ensure consistent parameters such as $C_{cuff}$.

22. The apparatus of 20, wherein the internal pressure sensor and a LED indicator are used to set proper initial pressure consistent measuring condition.

23. The apparatus of any one of 20-22, wherein the components are miniaturized into a wearable device for getting partial oscillometric waveforms, while the collection of full oscillometric waveforms for getting personalized parameters is done on a standalone device.

24. The apparatus of any one of 20-23, further comprising an add-on device with an additional pump and power supply, which collects full oscillometric waveforms for getting personalized parameters.

25. The apparatus of any one of 20-24, wherein the use of full oscillometric waveforms for calibration can be done at a very low frequency, while the wrist-worn band is worn for high-frequency blood pressure monitoring.

26. The apparatus of any one of 20-23, wherein the wrist-worn band has the power and pressure capacity to collect full or longer partial waveforms to calibrate on its own.

27. The apparatus of any one of 20-23, and 26, further comprising an additional power supply through batteries, through wireless charging or AC power to support the power needs of collecting full or partial waveforms for the device to calibrate on its own.

28. The apparatus of any one of 20-27, wherein blood pressure readings can be obtained through both full occlusion (analyzing the full oscillometric waveforms) and non-occlusion (analyzing the partial waveforms).

29. The apparatus of any one of 20-27, wherein blood pressure readings can be only obtained through the full occlusion mechanism, while the partial occlusion serves as passive monitoring of blood pressure variation.

30. The apparatus of 20, wherein non-occlusive blood pressure monitoring can be performed through a cuff-based blood pressure monitor, with improved comfort.

31. The apparatus of any one of 20-30, wherein the device can be made into applying around any arteries, such as around the arm, leg, neck, ankle, or fingers.

32. The apparatus of any one of 20-31, further comprising heart rate readings derived from counting the number of pulses in a given time.

33. The apparatus of any one of 20-29 and 31-32, further comprising motion sensors such as accelerometer and gyroscope to assist with the calibration of blood pressure to be at the heart level.

34. The band of 33, wherein the motion sensors are used to infer the activities of the users in order to assist with the interpretation of blood pressure data.

35. The apparatus of any one of 20-34, further comprising additional sensors, such as photoplethysmography (PPG), electrocardiogram (ECG), ultra wideband (UWB), temperature, galvanic skin sensor (GSR), respiratory monitoring, and bioimpedance to assist with the characterization and analysis of partial oscillometric waveforms.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A blood pressure monitoring device, comprising:
   a body portion having a size and structure to extend around an appendage of a user during use;
   a fluid bladder at least one of attached to or integral with said body portion and arranged to be able to apply pressure to an adjacent artery or vein of said user during use;
   a pressure actuator fluidly connected to said fluid bladder;
   a controller configured to provide control signals to said pressure actuator to fill said fluid bladder to selected pressures;
   a signal processor configured to communicate with said controller to receive signals indicating said selected pressures to which said fluid bladder is filled; and
   a pressure sensor arranged in operative contact with said fluid bladder to measure blood pressure waveforms plus bladder fluid pressure to provide a pressure waveform signal containing information regarding a relationship between vessel distention and transmural pressure, said pressure sensor being further configured to communicate with said signal processor to provide said pressure waveform signal to said signal processor,
   wherein said controller is configured to provide a plurality of selected pressures that are less than a mean arterial pressure of said user, and
   wherein said signal processor is configured to calculate blood pressure parameters using pressure waveform signals produced during application of said plurality of selected pressures that are less than said mean arterial pressure of said user.

2. The blood pressure monitoring device of claim 1, wherein said blood pressure parameters comprise at least systolic and diastolic blood pressures of said subject.

3. The blood pressure monitoring device of claim 2, wherein said controller is configured to provide said plurality of selected pressures such that all selected pressures are less than a diastolic blood pressure of said user.

4. The blood pressure monitoring device of claim 3, wherein said controller is configured to provide only selected pressures that are less than said diastolic blood pressure of said user.

5. The blood pressure monitoring device of claim 1, wherein said controller is configured to provide only selected pressures that are at least 20 mmHg and less than 40 mmHg.

6. The blood pressure monitoring device of claim 4, wherein said body portion is configured in a form of a ring to be worn by said user on a finger or toe for an extended period of substantially continuous blood pressure monitoring.

7. The blood pressure monitoring device of claim 4, further comprising:
   a wireless transmitter at least one of contained within, attached to, or integral with said body portion, said wireless transmitter being configured to communicate with said signal processor to transmit output signals comprising at least one of said calculated systolic and diastolic blood pressures, said pressure waveform signals, or signals based on said pressure waveform signals; and a battery at least one of contained within, attached to, or integral with said body portion, said battery being in electrical connection with said pressure actuator, said controller, and said signal processor, wherein said blood pressure monitoring device is wireless and sufficiently light and small to be worn by said user for extended periods of time.

8. The blood pressure monitoring device of claim 2, wherein said signal processor is configured to use a model in conjunction with said pressure waveform signals produced during said plurality of selected pressures to calculate said systolic and diastolic blood pressure.

9. The blood pressure monitoring device of claim 8, wherein said model is at least one of a pre-determined subject-specific model, a demographic-specific model, a generalized model based on a large scale population study, or a self-calibration model.

10. The blood pressure monitoring device of claim 2, further comprising at least one of an accelerometer or a gyroscope at least one of attached to, contained within or integral with said body portion, said at least one of said accelerometer or said gyroscope being further configured to communicate with said signal processor such that said signal processor can utilize at least one of motion, position or orientation information of said user for at least one of calculating said systolic and diastolic blood pressures or providing contextual information corresponding to calculated systolic and diastolic blood pressure.

11. The blood pressure monitoring device of claim 10, wherein said signal processor is configured to use a model in conjunction with said pressure waveform signals produced during said plurality of selected pressures and information from said at least one of said accelerometer or said gyroscope to calculate said systolic and diastolic blood pressures.

12. The blood pressure monitoring device of claim 11, wherein said model is at least one of a pre-determined subject-specific model, a demographic-specific model, a generalized model based on large scale population study, or a self-calibration model.

13. The blood pressure monitoring device of claim 4, wherein said body portion is configured in a form of a wrist band to be worn by said user on a wrist or an ankle for an extended period of substantially continuous blood pressure monitoring.

14. The blood pressure monitoring device of claim 4, further comprising at least one of an electro-cardiography (ECG) sensor, an ECG sensor and a photoplethysmography (PPG) sensor, an ultra wideband (UWB) sensor, a temperature sensor, a galvanic skin sensor (GSR), a respiratory monitoring sensor, or a bioimpedance sensor at least one of attached to, contained within or integral with said body portion, said at one of said ECG sensor, said ECG and PPG sensors, an ultra wideband (UWB) sensor, a temperature sensor, a galvanic skin sensor (GSR), a respiratory monitoring sensor, or a bioimpedance sensor being in communication with said signal processor, wherein said signal processor is further configured to extract pulse wave velocity information to be used in conjunction with information from said pressure waveform signals to calculate said systolic and diastolic blood pressures.

* * * * *